United States Patent
Aoki et al.

(10) Patent No.: US 9,677,096 B2
(45) Date of Patent: *Jun. 13, 2017

(54) MANUFACTURING METHOD FOR 1,4-BUTANEDIOL, MICROBE, AND GENE

(71) Applicant: SHOWA DENKO K.K., Tokyo (JP)

(72) Inventors: Hirobumi Aoki, Tokyo (JP); Yuzuru Kokido, Tokyo (JP); Yoko Hashimoto, Tokyo (JP); Tadashi Yoneda, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/440,116

(22) PCT Filed: Nov. 28, 2013

(86) PCT No.: PCT/JP2013/082068
§ 371 (c)(1),
(2) Date: May 1, 2015

(87) PCT Pub. No.: WO2014/087921
PCT Pub. Date: Jun. 12, 2014

(65) Prior Publication Data
US 2015/0376657 A1 Dec. 31, 2015

(30) Foreign Application Priority Data
Dec. 5, 2012 (JP) .................. 2012-266501

(51) Int. Cl.
  C12P 7/18 (2006.01)
  C12N 9/90 (2006.01)
  C12N 9/88 (2006.01)
  C12N 9/10 (2006.01)
  C12N 9/04 (2006.01)
  C12N 15/52 (2006.01)

(52) U.S. Cl.
  CPC .............. *C12P 7/18* (2013.01); *C12N 9/0006* (2013.01); *C12N 9/1029* (2013.01); *C12N 9/88* (2013.01); *C12N 9/90* (2013.01); *C12N 15/52* (2013.01); *C12Y 101/01035* (2013.01); *C12Y 101/01036* (2013.01); *C12Y 101/01157* (2013.01); *C12Y 203/01009* (2013.01); *C12Y 402/0112* (2013.01); *C12Y 402/01017* (2013.01); *C12Y 402/01055* (2013.01); *C12Y 402/01119* (2013.01); *C12Y 503/03003* (2013.01)

(58) Field of Classification Search
  None
  See application file for complete search history.

(56) References Cited

U.S. PATENT DOCUMENTS

| | | | |
|---|---|---|---|
| 5,981,257 A | 11/1999 | Fukui et al. | |
| 7,985,566 B2 | 7/2011 | Aoshima et al. | |
| 8,067,214 B2 | 11/2011 | Burk et al. | |
| 2007/0259411 A1 | 11/2007 | Bramucci et al. | |
| 2007/0269872 A1 | 11/2007 | Taguchi et al. | |
| 2009/0191593 A1 | 7/2009 | Burk et al. | |
| 2010/0112654 A1 | 5/2010 | Burk et al. | |
| 2010/0285549 A1 | 11/2010 | Muramatsu et al. | |
| 2010/0304453 A1 | 12/2010 | Trawick et al. | |
| 2010/0330635 A1 | 12/2010 | Burgard et al. | |
| 2011/0003344 A1 | 1/2011 | Burk et al. | |
| 2011/0045575 A1 | 2/2011 | Van Dien et al. | |
| 2011/0129899 A1 | 6/2011 | Haselbeck et al. | |
| 2011/0129904 A1 | 6/2011 | Burgard et al. | |

(Continued)

FOREIGN PATENT DOCUMENTS

EP 2511377 10/2012
JP H10-108682 4/1998

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
E. Okamura et al., Unprecedented acetoacetyl-coenzyme a synthesizing enzyme of the thiolase superfamily involved in the mevalonate pathway, PNAS (Proc. Natl. Acad. Sci.), vol. 107, No. 25, Jun. 22, 2010, pp. 11265-11270.
I. Miyahisa et al., Efficient production of (2S)-flavanones by *Escherichia coli* containing an artificial biosynthetic gene cluster, Appl Microbiol Biotechnol. 68: pp. 498-504 (2005).

(Continued)

*Primary Examiner* — Christian Fronda
(74) *Attorney, Agent, or Firm* — IPUSA, PLLC

(57) ABSTRACT

A method of manufacturing 1,4-butanediol through acetyl-CoA, acetoacetyl-CoA, 3-hydroxybutyryl-CoA, crotonyl-CoA, and 4-hydroxybutyryl-CoA by using a microbe and/or a culture thereof, wherein the microbe in the manufacturing method for 1,4-butanediol includes any one of genes among (a) a gene that has a base sequence of sequence number 1, (b) a gene that has a base sequence such that one or more bases are deleted, substituted, or added in a base sequence of sequence number 1, wherein the gene has a base sequence with an identity greater than or equal to 90% with respect to the base sequence of sequence number 1, and (c) a gene that hybridizes with a gene that has a base sequence complementary with a gene that has a base sequence described in sequence number 1 on a stringent condition, and includes any one or more genes among (d) genes that have base sequences of sequence numbers 2 to 9, (e) genes that have base sequences such that one or more bases are deleted, substituted, or added in base sequences of sequence numbers 2 to 9, wherein the genes have base sequences with an identity greater than or equal to 90% with respect to original base sequences thereof, and (f) genes that hybridize with genes that have base sequences complementary with genes that have base sequences of sequence numbers 2 to 9 on a stringent condition.

4 Claims, 1 Drawing Sheet

(56) References Cited

U.S. PATENT DOCUMENTS

| | | |
|---|---|---|
| 2011/0159572 A1 | 6/2011 | Burk et al. |
| 2011/0229946 A1 | 9/2011 | Haselbeck et al. |
| 2011/0281337 A1 | 11/2011 | Burk et al. |
| 2012/0208249 A1 | 8/2012 | Trawick et al. |
| 2012/0225463 A1 | 9/2012 | Van Dien et al. |
| 2012/0276606 A1 | 11/2012 | Okabayashi et al. |
| 2013/0029381 A1 | 1/2013 | Haselbeck et al. |
| 2013/0071883 A1 | 3/2013 | Burk et al. |
| 2013/0071886 A1 | 3/2013 | Burk et al. |
| 2013/0109069 A1 | 5/2013 | Burk et al. |
| 2013/0131262 A1 | 5/2013 | Burgard et al. |
| 2013/0189751 A1 | 7/2013 | Haselbeck et al. |

FOREIGN PATENT DOCUMENTS

| | | |
|---|---|---|
| JP | 2008-245633 | 10/2008 |
| JP | 2010-259388 | 11/2010 |
| JP | 2011-509691 | 3/2011 |
| JP | 2012-501678 | 1/2012 |
| JP | 2012-511928 | 5/2012 |
| JP | 2012-529267 | 11/2012 |
| WO | 2006/115226 | 11/2006 |
| WO | 2008/115840 | 9/2008 |
| WO | 2010/006076 | 1/2010 |
| WO | 2010/127319 | 11/2010 |
| WO | 2010/141920 | 12/2010 |
| WO | 2011/047101 | 4/2011 |
| WO | 2011/052718 | 5/2011 |
| WO | 2011/071682 | 6/2011 |
| WO | 2011/156794 | 12/2011 |

OTHER PUBLICATIONS

O. P. Peoples et al.,Poly-β-hydroxybutyrate Biosynthesis in Alcaligenes eutrophus H16. Characterization of the Genes Encoding β-Ketothiolase and Acetoacetyl-CoA Reductase., The Journal of Biological chemistry, vol. 264, No. 26, Issue of Sep. 15, pp. 15293-15297 (1989).
P. Friedrich et al., The Complete Stereochemistry of the Enzymatic Dehydration of 4-Hydroxybutyryl Coenzyme A to Crotonyl Coenzyme A., Angew. Chem. Int. Ed. 2008, 47, pp. 3254-3257 (2008).
G. J. Moskowitz et al., Metabolism of Poly-β-hydroxybutyrate. II. Enzymatic Synthesis of D-(-)-β-Hydroxybutyryl Coenzyme A by an Enoyl Hydrase from Rhodospirillum rubrum, Biochemistry, vol. 8, No. 7, Jul. 1969, pp. 2748-2755.
A. Gerhardt et al., Fermentation of 4-aminobutyrate by Clostridium aminobutyricum: cloning of two genes involved in the formation and dehydration of 4-hydroxybutyryl-CoA, Arch. Microbiol., 174, pp. 189-199 (2000).
K. Matsumoto et al., A New Pathway for Poly(3-hydroxybutyrate) Production in Escherichia coli and Corynebacterium glutamicum by Functional Expression of a New Acetoacetyl-coenzyme A Synthase, Biosci. Biotechnol. Biochem., 75 (2). pp. 364-366 (2011).
S. Wakil. et al., Fatty Acid Metabolism and Ketone Body Formation., Metabolism, vol. 11, No. 8 (Aug.), pp. 742-761(1962).
International Search Report mailed on Nov. 26, 2013 issued with respect to the international patent application No. PCT/JP2013/072186.
Database GenBank [online], Accession No. AB540131, <http://www.ncbi.nlm.nih.gov/nuccore/AB540131> Oct. 9, 2013 uploaded, [retrieved on Mar. 27, 2015] E. Okamura et al., Definition: Streptomyces sp. CL190 nphT7 gene for acetyl-CoA:malonyl-CoA acyltransferase, complete cds.
Database GenBank [online], Accession No. YP_224999, <http://www.ncbi.nlm.nih.gov/protein/YP_224999.1?report=genpept> Dec. 16, 2014 uploaded, [retrieved on Mar. 27, 2015] M. Follmann et al., Definition: acetyl/propionyl-COA carboxylase subunit beta [Corynebacterium glutamicum ATCC 13032].
Database GenBank [online], Accession No. CCH23890, <http://www.ncbi.nlm.nih.gov/protein/CCH23890> Feb. 27, 2015 uploaded, [retrieved on Mar. 27, 2015] S. Binder et al., Definition: acyl-CoA carboxylase [Corynebacterium glutamicum K051].
Database GenBank [online], Accession No. AJ250267, <http://www.ncbi.nlm.nih.gov/nuccore/AJ250267> May 13, 2008 uploaded, [retrieved on Mar. 27, 2015] A. Gerhardt et al., Definition: Clostridium aminobutyricum abfD gene, abfT gene and abfH gene (partial) for dehydration of 4-hydroxybutyrate.
Database GenBank [online], Accession No. AY620821, <http://www.ncbi.nlm.nih.gov/nuccore/AY620821> Jun. 27, 2004 uploaded, [retrieved on Apr. 24, 2015] J. Toth et al., Definition: Clostridium beijerinckii strain NRRL B592 conserved hypothetical protein gene, partial cds; and acetone and butanol production operon, complete sequence.
Database GenBank [online], GenBank gi No. 1116040, <http://www.ncbi.nlm.nih.gov/nucest/1116040> Dec. 13, 1995 Entry Created, Aug. 14, 2006 Last Updated, [retrieved on Mar. 27, 2015] Y. Kohara, CELK070C7R Yuji Kohara unpublished cDNA Caenorhabditis elegans cDNA clone yk70c7 3-, mRNA sequence.
Zha et al. "Improving cellular malonyl-CoA level in Escherichia coli via metabolic engineering", Metabolic Engineer. 11:192-198, 2009.
Office Action mailed on Feb. 17, 2016 issued with respect to the related U.S. Appl. No. 14/429,453.
H. Yim et al., Metabolic engineering of Escherichia coli for direct production of 1,4-butanediol, Nature Chemical Biology, vol. 7, Jul. 2011, pp. 445-452.
International Search Report mailed on Jan. 14, 2014.
An-Ping Zeng et al: "Microbial production of diols as platform chemicals: Recent progresses", Current Opinion in Biotechnology, vol. 22, No. 6, May 1, 2011(May 1, 2011), pp. 749-757, XP028397461, ISSN: 0958-1669, DOI: 10.1016/J.COPBIO.2011.05.005 [retrieved on May 19, 2011] *p. 754.*.
Database Geneseq [Online] Sep. 29, 2011 (Sep. 29, 2011), "C. acetobutylicum ATCC 824 acetyl-CoA acetyltransferase, Seq ID 4.", XP002757601, retrieved from EBI accession No. GSP:AZM02723 Database accession No. AZM02723*sequence*.
Dana M. Francis et al., Strategies to Optimize Protein Expression in E. coli, Current Protocols in Protein Science pp. 5.24.1-5.24.29, Aug. 2010, Published online Aug. 2010 in Wiley Interscience (www.interscience.wiley.com) DOI: 10.1002/0471140864.ps0524s61.
Database GenBank [online], Accession No. AF072735.1, <http://www.ncbi.nlm.nih.gov/nuccore/af072735.1> Aug. 16, 2001 uploaded, [retrieved on May 23, 2016] P. Durre et al., Definition: Clostridium acetobutylicum ThIR (thIR) and thiolase B (thIB) genes, complete cds; ThIC (thIC) gene, partial cds; and unknown gene.
Database GenBank [online], Accession No. AM260479.1, <http://www.ncbi.nlm.nih.gov/nuccore/AM260479.1> Mar. 7, 2015 uploaded, [retrieved on May 23, 2016] A. Pohlmann, et al., Definition: Ralstonia eutropha H16 chromosome 1.
Database GenBank [online], Accession No. AY665302, <http://www.ncbi.nlm.nih.gov/nuccore/AY665302> Jan. 28, 2005 uploaded, [retrieved on May 23, 2016] X. Lu, et al., Definition: Aeromonas hydrophila strain WQ PHA granule-associated protein (phaP), PHA synthase (phaC), and enoyl-CoA hydratase (phaJ) genes, complete cds.
Database GenBank [online], Accession No. AF157306, <http://www.ncbi.nlm.nih.gov/nuccore/AF157306> May 17, 2004 uploaded, [retrieved on May 23, 2016] J. Toth, et al., Definition: Clostridium beijerinckii strain NRRL B593 hpothetical protein, coenzyme a acylating aldehyde dehydrogenase (ald), acetoacetate:butyrate/acetate coenzyme a transferase (ctfA), acetoacetate:butyrate/acetate coenzyme a transferase (ctfB), and acetoacetate decarboxylase (adc) genes, complete cds.
Database GenBank [online], Accession No. AF321779.1, <http://www.ncbi.nlm.nih.gov/nuccore/AF321779.1> Jan. 17, 2002 uploaded, [retrieved on May 23, 2016] L. Fontaine, et al., Definition: Clostridium acetobutylicum plasmid pSOL1 aldehyde/alcohol dehydrogenase (adhE2) gene, complete cds.
Database GenBank [online], Accession No. U17110.1, <http://www.ncbi.nlm.nih.gov/nuccore/U17110.1> Apr. 4, 1996 uploaded, [retrieved on May 23, 2016] Z.L. Boynton, et al., Definition:

(56) References Cited

OTHER PUBLICATIONS

Clostridium acetobutylicum crotonase (crt), putative butyryl-CoA dehydrogenase (BCD), putative a-subunit of electron-transfer flavoprotein (etfA), putative b-subunit of electron-transfer flavoprotein (etfB), and 3-hydroxybutyryl-CoA dehydrogenase (hbd) genes, complete cds.
T. Fukui et al., Expression and Characterization of (R)-Specific Enoyl Coenzyme a Hydratase Involved in Polyhydroxyalkanoate Biosynthesis by Aeromonas caviae, Journal of Bacteriology, vol. 180, No. 3, Feb. 1998, pp. 667-673.
E. I. Lan et al., ATP drives direct photosynthetic production of 1-butanol in *cyanobacteria*, PNAS (Proc. Natl. Acad. Sci.), vol. 109, No. 16, Apr. 17, 2012, pp. 6018-6023.
V. K. Madan et al., Purification and Properties of NADP-Dependent L(+)-3-Hydroxybutyryl-CoA Dehydrogenase from Clostridium kluyveri, Eur. J. Biochem., vol. 32, 1973, pp. 51-56.
H. Seedorf et al., The genome of Clostridium kluyveri, a strict anaerobe with unique metabolic features, PNAS (Proc. Natl. Acad. Sol.), vol. 105, No. 6, Feb. 12, 2008, pp. 2128-2133.
M. Inui et al., Expression of Clostridium acetobutylicum butanol synthetic genes in *Escherichia coli*, Appl. Microbiol. Biotechnol., vol. 77, 2008, pp. 1305-1316.
International Search Report mailed on Oct. 29, 2013 issued with respect to the international patent application No. PCT/JP2013/075513.
Office Action mailed on Apr. 27, 2016 issued with respect to the related U.S. Appl. No. 14/440,117.
Office Action mailed on Oct. 20, 2016 issued with respect to the related U.S. Appl. No. 14/429,459.

\* cited by examiner

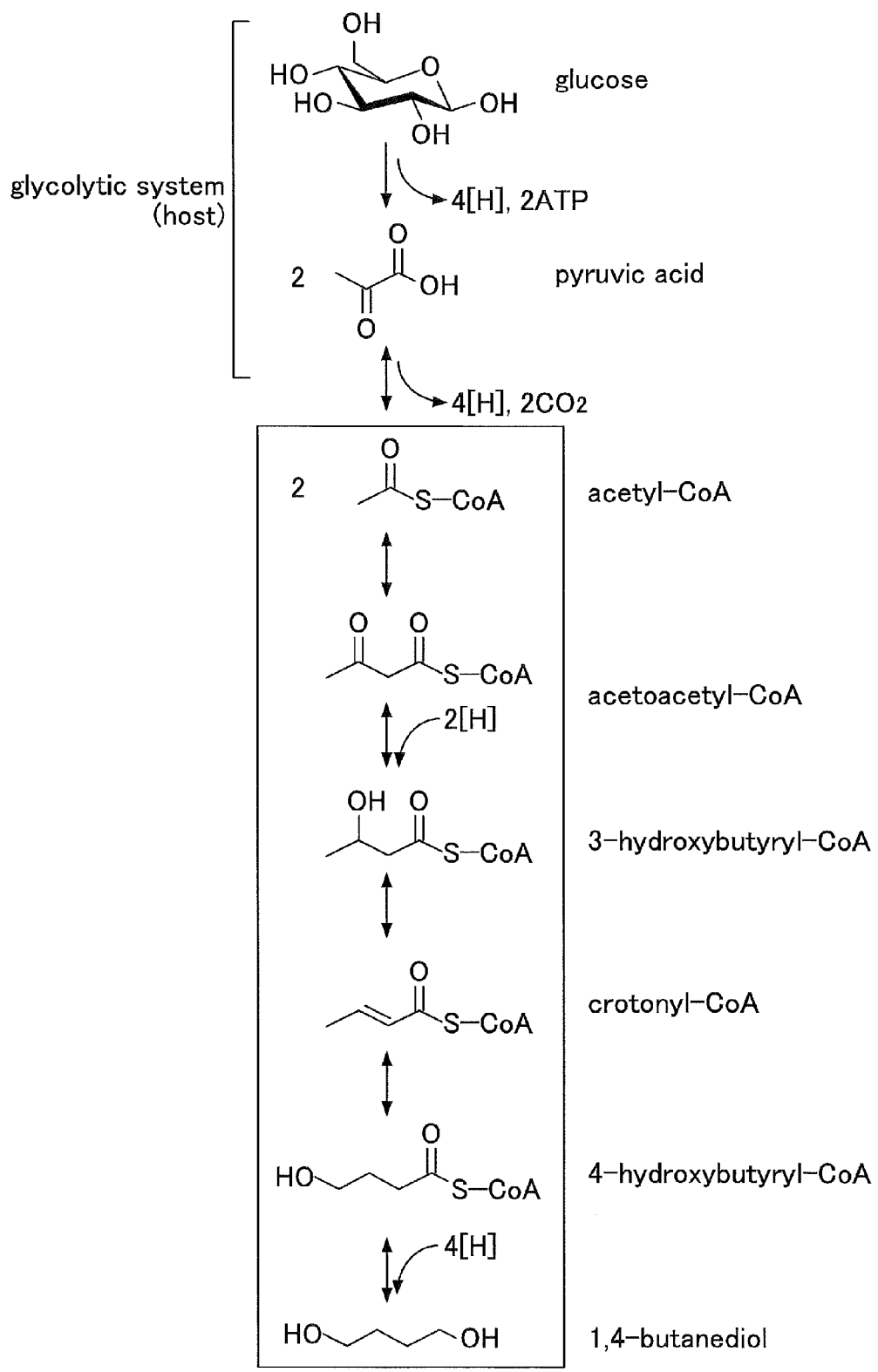

MANUFACTURING METHOD FOR 1,4-BUTANEDIOL, MICROBE, AND GENE

INCORPORATION BY REFERENCE

The 30,069 byte text file titled "SequenceListing2.txt" (Creation Date: Aug. 20, 2015) is hereby incorporated by reference.

TECHNICAL FIELD

The present invention relates to a manufacturing method for 1,4-butanediol, a microbe, and a gene.

BACKGROUND ART

In recent years, attention is paid to a compound manufacturing process with a renewable source as a raw material from the viewpoint of depletion of fossil resource, a countermeasure for global warming, or the like. In particular, a so-called bio-refinery has widely been studied wherein a variety of compounds as raw materials for a polymer or compounds as raw materials for a chemical product are manufactured in biochemical processes with biomass as raw materials.

For a compound that is expected for raw material conversion of biomass, 1,4-butanediol is provided. 1,4-butanediol is widely used as a synthetic raw material for a precision organic chemical product, monomer units of a polyester and an engineering plastic, or the like, and a market size thereof is large. For that reason, demand for a method of manufacturing 1,4-butanediol efficiently in a biochemical process with a renewable source such as biomass as a raw material is increased.

For manufacturing methods for 1,4-butanediol that use a biochemical process, there are provided, for example, methods described in patent documents 1 and 2 and non-patent document 1.

PRIOR ART DOCUMENTS

[Patent Document 1] Japanese Patent No. 4380704 specification

[Patent Document 2] International Publication No. 2008/115840 official gazette

[Non-patent document 1] Harry Yim et al., Metabolic engineering of *Escherichia coli* for direct production of 1,4-butanediol, Nature Chemical Biology, 7, 445-452 (2011).

DISCLOSURE OF THE INVENTION

Problems to be Solved by the Invention

However, methods described in patent documents 1 and 2 and non-patent document 1 are complicated processes.

Against a problem as described above, there is provided a new manufacturing method for 1,4-butanediol that is capable of obtaining 1,4-butanediol economically.

Means for Solving the Problem

The present invention includes the following.

[1] A method of manufacturing 1,4-butanediol by using a microbe and/or a culture thereof, through the following processes:

(1) a process of converting acetyl-CoA into acetoacetyl-CoA;

(2) a process of converting acetoacetyl-CoA into 3-hydroxybutyryl-CoA;

(3) a process of converting 3-hydroxybutyryl-CoA into crotonyl-CoA;

(4) a process of converting crotonyl-CoA into 4-hydroxybutyryl-CoA; and (5) a process of converting 4-hydroxybutyryl-CoA into 1,4-butanediol, wherein the microbe in the manufacturing method for 1,4-butanediol includes any one of genes among:

(a) a gene that has a base sequence of sequence number 1;

(b) a gene that has a base sequence such that one or more bases are deleted, substituted, or added in a base sequence of sequence number 1, wherein the gene has a base sequence with an identity greater than or equal to 90% with respect to the base sequence of sequence number 1; and (c) a gene that hybridizes with a gene that has a base sequence complementary with a gene that has a base sequence described in sequence number 1 on a stringent condition;

as a gene that codes an enzyme that catalyzes a process of (4) described above; and includes any one or more genes among:

(d) a gene that has a base sequence of any one of sequence numbers 2 to 9;

(e) a gene that has a base sequence such that one or more bases are deleted, substituted, or added in a base sequence of any one of sequence numbers 2 to 9, wherein the gene has a base sequence with an identity greater than or equal to 90% with respect to an original base sequence thereof; and (f) a gene that hybridizes with a gene that has a base sequence complementary with a gene that has a base sequence of any one of sequence numbers 2 to 9 on a stringent condition;

as a gene that codes an enzyme that catalyzes any one of processes of (1)-(3) and (5) described above.

[2] A microbe that has a capability of manufacturing 1,4-butanediol through the following processes:

(1) a process of converting acetyl-CoA into acetoacetyl-CoA;

(2) a process of converting acetoacetyl-CoA into 3-hydroxybutyryl-CoA;

(3) a process of converting 3-hydroxybutyryl-CoA into crotonyl-CoA;

(4) a process of converting crotonyl-CoA into 4-hydroxybutyryl-CoA; and (5) a process of converting 4-hydroxybutyryl-CoA into 1,4-butanediol, wherein the microbe includes any one of genes among:

(a) a gene that has a base sequence of sequence number 1;

(b) a gene that has a base sequence such that one or more bases are deleted, substituted, or added in a base sequence of sequence number 1, wherein the gene has a base sequence with an identity greater than or equal to 90% with respect to the base sequence of sequence number 1; and (c) a gene that hybridizes with a gene that has a base sequence complementary with a gene that has a base sequence described in sequence number 1 on a stringent condition;

as a gene that codes an enzyme that catalyzes a process of (4) described above; and includes any one or more genes among:

(d) a gene that has a base sequence of any one of sequence numbers 2 to 9;

(e) a gene that has a base sequence such that one or more bases are deleted, substituted, or added in a base sequence of any one of sequence numbers 2 to 9, wherein the gene has a base sequence with an identity greater than or equal to 90% with respect to an original base sequence thereof; and (f) a gene that hybridizes with a gene that has a base sequence complementary with a gene that has a base sequence of any one of sequence numbers 2 to 9 on a stringent condition;

as a gene that codes an enzyme that catalyzes any one of processes of (1)-(3) and (5) described above.

[3] The gene to be used in the manufacturing method for 1,4-butanediol described in [1], which is a gene described in any one of under-mentioned (a)-(c):

(a) a gene that has a base sequence of any one of sequence numbers 1 to 9

(b) a gene that has a base sequence such that one or more bases are deleted, substituted, or added in a base sequence of any one of sequence numbers 1 to 9, wherein the gene has a base sequence with an identity greater than or equal to 90% with respect to an original base sequence thereof (c) a gene that hybridizes with a gene that has a base sequence complementary with a gene that has a base sequence of any one of sequence numbers 1 to 9 on a stringent condition.

Effects of the Invention

It is possible to provide a new manufacturing method for 1,4-butanediol that is capable of obtaining 1,4-butanediol economically.

BRIEF DESCRIPTION OF THE DRAWINGS

FIG. 1 is one example of an enzymatic system of a manufacturing method for 1,4-butanediol according to the present embodiment.

BEST MODE FOR IMPLEMENTING THE INVENTION

The present invention will be described in detail below. Here, "CoA" in the present specification means "coenzyme A". Furthermore, "%" indicates "% by mass" unless otherwise described. "ppm" is a mass standard.

A manufacturing method for 1,4-butanediol according to an embodiment is a manufacturing method for 1,4-butanediol that relies on an enzyme reaction that uses a microbe or a culture thereof, through acetyl-CoA, acetoacetyl-CoA, 3-hydroxybutyryl-CoA, crotonyl-CoA, and 4-hydroxybutyryl-CoA.

Specifically, each enzyme reaction includes:

(1) a process of converting acetyl-CoA into acetoacetyl-CoA;

(2) a process of converting acetoacetyl-CoA into 3-hydroxybutyryl-CoA;

(3) a process of converting 3-hydroxybutyryl-CoA into crotonyl-CoA;

(4) a process of converting crotonyl-CoA into 4-hydroxybutyryl-CoA; and (5) a process of converting 4-hydroxybutyryl-CoA into 1,4-butanediol.

The present inventors executed a variety of studies in order to improve productivity of 1,4-butanediol, and as a result, found that it was possible to obtain 1,4-butanediol at a high productivity by using a particular gene or a homolog thereof in a gene that codes an enzyme that catalyzes each reaction in a process as described above.

For a particular gene as described previously, specifically, any one of genes among:

(a) a gene that has a base sequence of sequence number 1;

(b) a gene that has a base sequence such that one or more bases are deleted, substituted, or added in a base sequence of sequence number 1, wherein the gene has a base sequence with an identity greater than or equal to 90% with respect to the base sequence of sequence number 1; and (c) a gene that hybridizes with a gene that has a base sequence complementary with a gene that has a base sequence described in sequence number 1 on a stringent condition;

is preferably used as a gene that codes an enzyme that catalyzes a reaction in (4) a process of converting crotonyl-CoA into 4-hydroxybutyryl-CoA.

Furthermore, any one of genes among:

(a) a gene that has a base sequence of any one of sequence numbers 2 to 9;

(b) a gene that has a base sequence such that one or more bases are deleted, substituted, or added in a base sequence of any one of sequence numbers 2 to 9, wherein the gene has a base sequence with an identity greater than or equal to 90% with respect to a base sequence of sequence number 1; and (c) a gene that hybridizes with a gene that has a base sequence complementary with a gene that has a base sequence of any one of sequence numbers 2 to 9 on a stringent condition;

is preferably used as a gene that codes an enzyme that catalyzes a corresponding conversion reaction in any one or more processes among other processes (1), (2), (3), and (5).

In the present embodiment, a particular gene as described above includes a gene that has a base sequence that is specifically indicated in a sequence listing, and a homolog thereof. A homolog includes an ortholog and a paralog. An ortholog refers to a set of corresponding genes among species generated from a gene of a common ancestor by means of speciation and enzymes obtained from such genes. A paralog refers to corresponding genes among species generated by means of not speciation but gene duplication in an identical species and enzymes obtained from such genes. A homolog refers to genes that have an identity in sequences thereof, regardless of an ortholog or a paralog, and enzymes obtained from such genes.

More specifically, a homolog (gene) of a gene as described above refers to a gene that has a base sequence with an identity greater than or equal to 90%, preferably an identity greater than or equal to 95%, with respect to such a gene, and more preferably, a gene that is completely identical to such a gene or wherein one or several bases thereof are deleted, substituted, or added.

Furthermore, a homolog gene includes a gene that hybridizes with a gene that has a base sequence complementary with a target gene on a stringent condition. Specifically, it is possible to acquire a gene or an enzyme that is obtained by transformation caused by such a gene, by applying a homology retrieval program (for example, BLAST or FASTA) to a publicly-known data base, or based on an ordinary method such as hybridization or polymerase chain reaction (PCR) on a stringent condition that uses a probe that is composed of at least a portion of an identified gene (DNA that is composed of a base sequence complementary with DNA that is composed of a base sequence of such a gene). Furthermore, it is possible for a person(s) skilled in the art to execute self-design by substituting a base sequence or the like. Here, for a stringent condition referred herein, there is provided, for example, a condition for executing hybridization described in a non-patent document of Molecular Cloning—A LABORATORY MANUAL THIRD EDITION (Joseph Sambrook, David W. Russell, Cold Spring Harbor Laboratory Press). More specifically, a hybridizing condition is a condition that retention with a probe in a solution that contains 6×SSC (a composition of 1×SSC: 0.15 M of sodium chloride, 0.015 M of sodium citrate, pH: 7.0), 0.5% of SDS, 5× Denhardt's solution, and 100 mg/mL of herring sperm DNA, at a constant temperature of 65° C. for 8-16 hours is executed to cause hybridization.

In the present invention, for example, a reaction is caused to proceed, by expressing (that may be co-expressing) an enzyme or a series or group of enzymes that is/are coded by each gene, that is selected as described above, in a body of a microbe provided in such a manner that a host microbe as described below is transformed by means of gene recombination.

A feature of a microbe that is used in the present embodiment, a fabrication method for the microbe, a method of use of the microbe (that is, a manufacturing method for 1,4-butanediol), an acquisition method of manufactured 1,4-butanediol, and the like, will be described below.

(A Host Microbe)

A host microbe that is used in the present embodiment is a host microbe that is capable of introducing a variety of genes as described below, and for example, it is possible to apply a gene recombination technique to a host microbe.

An example of a host microbe that is capable of introducing a gene as described above in the present embodiment is not particularly limited as long as it is possible to apply a gene recombination technique to such a microbe. From the viewpoint of industrial availability, there is provided *Escherichia coli*, a yeast, a coryneform bacteria, or a clostridial bacteria, as a specific example. For a yeast, there is provided *Saccharomyces cerevisiae, Schizosaccharomyces pombe, Kluyveromyces lactis, Kluyveromyces marxianus*, or the like. For a coryneform bacteria, there is provided, *Corynebacterium glutamicum, Corynebacterium efficiens, Brevibacterium divaricatum, Brevibacterium saccharolyticum, Brevibacterium immariophilum, Brevibacterium lactofermentum, Brevibacterium roseum, Brevibacterium flavum, Brevibacterium thiogenitalis, Corynebacterium acetoacidophilum, Corynebacterium acetoglutamicum, Corynebacterium callunae, Corynebacterium lilium, Corynebacterium mellassecola, Microbacterium ammoniaphilum*, or the like. For a clostridial bacteria, there is provided *Clostridium kluyveri, Clostridium acetobutylicum, Clostridium aminobutyricum, Clostridium beijerinckii, Clostridium saccharoperbutylacetonicum*, or the like. Among these, it is preferable to use *Escherichia coli, Saccharomyces cerevisiae, Schizosaccharomyces pombe*, or *Corynebacterium glutamicum*, because transformation thereof is easy, and it is more preferable to use *Escherichia coli*.

Furthermore, a transformed microbe in the present embodiment may be used as a microbe culture bacterial body itself or a variety of forms of a culture thereof. Specifically, a culture of a microbe in the present embodiment includes a suspension of a microbe culture bacterial body in a medium such as a culture medium or a buffer solution, a cell-free extracted fluid from a microbe culture bacterial body, and further, a product processed by concentrating, purifying, and extracting a component that catalyzes such a reaction from such a cell-free extracted fluid or the like. A culture of a microbe in the present embodiment further includes the above-mentioned processed product of a microbe that is fixed on a poorly soluble carrier. For such a fixation carrier, there is provided a compound that forms a poorly water-soluble solid content that encloses a microbial or bacterial body as described previously or a processed product thereof, such as polyacrylamide, polyvinyl alcohol, poly-N-vinylformamide, polyallylamine, polyethyleneimine, methylcellulose, glucomannan, alginate, or carrageenan, or further a copolymer or crosslinked product thereof, or the like. One kind of these may be used singly or two or more kinds thereof may be mixed and used. Furthermore, it is also possible to use, as a culture of a microbe, a microbe or an extracted fluid or extracted component thereof that is held on an object that is preliminarily formed as a solid, such as activated carbon, a porous ceramic, glass fiber, a porous polymer molded object, or a nitrocellulose film.

(A Transformed Microbe)

A host microbe that is used in the present embodiment is a host microbe that is capable of introducing a variety of genes as described below, wherein it is possible to apply, for example, a gene recombination technique to such a host microbe. Specifically, such a host microbe further has each enzyme system of an enzyme reaction system that is capable of producing 1,4-butanediol through acetyl-CoA, acetoacetyl-CoA, 3-hydroxybutyryl-CoA, crotonyl-CoA, and 4-hydroxybutyryl-CoA, in addition to an enzyme system that is intrinsically possessed thereby. An enzyme system in a manufacturing method for 1,4-butanediol according to the present embodiment and a gene that codes each enzyme system will be described below.

FIG. 1 illustrates one example of an enzyme system in a manufacturing method for 1,4-butanediol according to the present embodiment. In the present embodiment, it is possible to obtain 1,4-butanediol by using a culture that is expressed in a microbial body by transforming a series of genes as described below or the like. Here, a gene is inserted into an arbitrary vector individually or as a series of clusters so that a host microbe is transformed. An obtained transformed body is cultured in a culture medium with an appropriate carbon source, for example, glucose as a carbon source, so that each gene is expressed. In a case of a gene capable of being constitutively expressed in a host, a transformed body is cultured in a culture medium so that such a gene is expressed. On the other hand, in a case where each gene is constituted under a control of a regulator disposed on a vector, an inducible substrate is added to transfer to inductive environment, and thereby, each coding gene is expressed. Here, culturing in the present embodiment includes all of culturing conditions for a normal microbe culturing, and further, culturing in the present embodiment means that a microbe is cultured for a period of time and a condition enough to manufacture 1,4-butanediol.

[A Gene that Catalyzes a Reaction that Converts Acetyl-CoA into Acetoacetyl-CoA]

For a gene that codes an enzyme that catalyzes a reaction that converts acetyl-CoA into acetoacetyl-CoA in the present embodiment, (a) a gene that has a base sequence of sequence number 2;

(b) a gene that has a base sequence such that one or more bases are deleted, substituted, or added in a base sequence of sequence number 2, wherein the gene has a base sequence with an identity greater than or equal to 90% with respect to the base sequence of sequence number 2; or (c) a gene that hybridizes with a gene that has a base sequence complementary with a gene that has a base sequence described in sequence number 2 on a stringent condition;

is preferably used that is provided by the inventors.

Furthermore, for a gene that codes an enzyme that catalyzes a reaction that converts acetyl-CoA into acetoacetyl-CoA in the present embodiment, (a) a gene that has a base sequence of sequence number 3;

(b) a gene that has a base sequence such that one or more bases are deleted, substituted, or added in a base sequence of sequence number 3, wherein the gene has a base sequence with an identity greater than or equal to 90% with respect to the base sequence of sequence number 3; or (c) a gene that hybridizes with a gene that has a base sequence complementary with a gene that has a base sequence described in sequence number 3 on a stringent condition;

is preferably used that is provided by the inventors.

[A Gene that Catalyzes a Reaction that Converts Acetoacetyl-CoA into 3-hydroxybutyryl-CoA]

For a gene that codes an enzyme that catalyzes a reaction that converts acetoacetyl-CoA into 3-hydroxybutyryl-CoA in the present embodiment, (a) a gene that has a base sequence of sequence number 4;

(b) a gene that has a base sequence such that one or more bases are deleted, substituted, or added in a base sequence of sequence number 4, wherein the gene has a base sequence with an identity greater than or equal to 90% with respect to the base sequence of sequence number 4; or (c) a gene that hybridizes with a gene that has a base sequence complementary with a gene that has a base sequence described in sequence number 4 on a stringent condition;

is preferably used that is provided by the inventors.

Furthermore, for a gene that codes an enzyme that catalyzes a reaction that converts acetoacetyl-CoA into 3-hydroxybutyryl-CoA in the present embodiment, (a) a gene that has a base sequence of sequence number 5;

(b) a gene that has a base sequence such that one or more bases are deleted, substituted, or added in a base sequence of sequence number 5, wherein the gene has a base sequence with an identity greater than or equal to 90% with respect to the base sequence of sequence number 5; or (c) a gene that hybridizes with a gene that has a base sequence complementary with a gene that has a base sequence described in sequence number 5 on a stringent condition;

is preferably used that is provided by the inventors.

[A Gene that Codes an Enzyme that Catalyzes a Reaction that Converts 3-hydroxybutyryl-CoA into Crotonyl-CoA]

For a gene that codes an enzyme that catalyzes a reaction that converts 3-hydroxybutyryl-CoA into crotonyl-CoA in the present embodiment, (a) a gene that has a base sequence of sequence number 6;

(b) a gene that has a base sequence such that one or more bases are deleted, substituted, or added in a base sequence of sequence number 6, wherein the gene has a base sequence with an identity greater than or equal to 90% with respect to the base sequence of sequence number 6; or (c) a gene that hybridizes with a gene that has a base sequence complementary with a gene that has a base sequence described in sequence number 6 on a stringent condition;

is preferably used that is provided by the inventors.

Furthermore, for a gene that codes an enzyme that catalyzes a reaction that converts 3-hydroxybutyryl-CoA into crotonyl-CoA in the present embodiment, (a) a gene that has a base sequence of sequence number 7;

(b) a gene that has a base sequence such that one or more bases are deleted, substituted, or added in a base sequence of sequence number 7, wherein the gene has a base sequence with an identity greater than or equal to 90% with respect to the base sequence of sequence number 7; or (c) a gene that hybridizes with a gene that has a base sequence complementary with a gene that has a base sequence described in sequence number 7 on a stringent condition;

is preferably used that is provided by the inventors.

[A Gene that Codes an Enzyme that Catalyzes a Reaction that Converts Crotonyl-CoA into 4-hydroxybutyryl-CoA]

For a gene that codes an enzyme that catalyzes a reaction that converts crotonyl-CoA into 4-hydroxybutyryl-CoA in the present embodiment, (a) a gene that has a base sequence of sequence number 1;

(b) a gene that has a base sequence such that one or more bases are deleted, substituted, or added in a base sequence of sequence number 1, wherein the gene has a base sequence with an identity greater than or equal to 90% with respect to the base sequence of sequence number 1; or (c) a gene that hybridizes with a gene that has a base sequence complementary with a gene that has a base sequence described in sequence number 1 on a stringent condition;

is preferably used that is provided by the inventors.

[A Gene that Codes an Enzyme that Catalyzes a Reaction that Converts 4-hydroxybutyryl-CoA into 1,4-butanediol]

For a gene that codes an enzyme that catalyzes a reaction that converts 4-hydroxybutyryl-CoA into 1,4-butanediol in the present embodiment, (a) a gene that has a base sequence of sequence number 8;

(b) a gene that has a base sequence such that one or more bases are deleted, substituted, or added in a base sequence of sequence number 8, wherein the gene has a base sequence with an identity greater than or equal to 90% with respect to the base sequence of sequence number 8; or (c) a gene that hybridizes with a gene that has a base sequence complementary with a gene that has a base sequence described in sequence number 8 on a stringent condition;

is preferably used that is provided by the inventors.

Furthermore, for a gene that codes an enzyme that catalyzes a reaction that converts 4-hydroxybutyryl-CoA into 1,4-butanediol in the present embodiment, (a) a gene that has a base sequence of sequence number 9;

(b) a gene that has a base sequence such that one or more bases are deleted, substituted, or added in a base sequence of sequence number 9, wherein the gene has a base sequence with an identity greater than or equal to 90% with respect to the base sequence of sequence number 9; or (c) a gene that hybridizes with a gene that has a base sequence complementary with a gene that has a base sequence described in sequence number 9 on a stringent condition;
is preferably used that is provided by the inventors.

Here, an enzyme that is coded by a gene as described above catalyzes a reaction that converts 4-hydroxybutyryl-CoA into 4-hydroxybutanal, and 1,4-butanediol is substantially and immediately derived from obtained 4-hydroxybutanal by an alcohol reductase that is normally possessed by a host microbe as described previously.

[Supply of Acetyl-CoA]

A supply method for acetyl-CoA that is a substrate in a manufacturing method for 1,4-butanediol according to the present embodiment is not particularly limited and a variety of known methods are used. For example, it is possible to be obtained from a saccharide such as glucose due to a glycolytic system of a host microbe. Furthermore, it is also possible to obtain acetyl-CoA in a pathway of β-oxidation of a lipid. Moreover, acetyl-CoA may be supplied by using a CoA transferase in such a manner that CoA is transferred to acetic acid by means of coupling with an appropriate CoA material.

(A Fabrication Method for a Microbe)

It is possible to execute introduction of a gene into a host microbe by appropriately combining and using a variety of known methods, for example, a method based on a restriction enzyme/ligation, an In-Fusion cloning method, and the like, so that a gene as described above or a part thereof is linked with an appropriate vector and an obtained recombinant vector is introduced into a host in such a manner that it is possible for a target gene to be expressed. Alternatively, it is possible to insert a target gene or a part thereof at an arbitrary position on genome by means of homologous recombination. A "part" refers to a part of each gene that is capable of expressing a protein that is coded by each gene in a case of being introduced into a host. A gene in the present invention encompasses DNA and RNA, and preferably, is DNA.

A vector that is linked with a gene as described previously is not particularly limited as long as it is possible to execute replication thereof in a host, and there are provided, for example, a plasmid, a phage, a cosmid, and the like, that are utilized for introduction of an exotic gene into *Escherichia coli*. For a plasmid, there is provided, for example, pHSG398, pUC18, pBR322, pSC101, pUC19, pUC118, pUC119, pACYC117, pBluescript II SK(+), pET17b, pET-Duet-1, pACYCDuet-1, pCDFDuet-1, pRSFDuet-1, pCO-LADuet-1, or the like, and for a phage, there is provided, for example, λgt10, Charon 4A, EMBL-, M13mp18, M13mp19, or the like. Some of them are commercially available and it is possible to use a commercially available product (kit) directly in accordance with, or by appropriately modifying, a procedure manual thereof.

In a vector as described above, an appropriate expression promoter may be connected to such a gene upstream thereof so that an inserted gene is expressed reliably. An expression promoter to be used is not particularly limited, and it is possible for a person skilled in the art to make an appropriate selection thereof depending on a host. For example, it is also possible to utilize T7 promoter, lac promoter, trp promoter, trc promoter, or λ-PL promoter that is utilized for expression of an exotic gene in *Escherichia coli*, or an Nar promoter region of a nitrate reduction gene nar GHJI operon that is derived from *Escherichia coli* and involved with nitrate respiration, or a promoter region of Frd gene that is a gene of a nitrate reductase of *Escherichia coli*.

Furthermore, depending on a case, it is also preferable to destruct an intrinsic gene of a host microbe so that such a gene is not expressed. For a method of gene destruction, it is possible to use a publicly-known method that is utilized for gene destruction in *Escherichia coli*. Specifically, it is possible to use a method that is used for fabricating a knockout cell or the like in such a technical field, such as a method (gene targeting method) that destructs such a gene by using a vector (targeting vector) that causes homologous recombination at an arbitrary position of a target gene, a method (gene trap method) that inserts a trap vector (reporter gene that does not have a promoter) at an arbitrary position of a target gene to destruct such a gene and be caused to lose a function thereof, or a method of a combination thereof.

A position that causes homologous substitution or a position for inserting a trap vector is not particularly limited as long as such a position is to cause mutation that eliminates expression of a target gene to be destructed, and is preferably a transcription control region.

Moreover, a method for introduction of a vector as described previously into a host is not particularly limited, and it is possible to provide, for example, a method that uses a calcium ion, a protoplast method, an electroporation method, or the like, that is generally utilized for introduction of a vector into *Escherichia coli*.

A target gene together with a promoter is inserted into a sequence homologous to a sequence on a genome and such a nucleic acid fragment is introduced into a cell by means of electroporation to cause homologous recombination, so that it is possible to practice a method that inserts a target gene at an arbitrary position on a genome by means of homologous recombination. As a nucleic acid fragment wherein a drug resistance gene is linked with a target gene is used in a case of introduction into a genome, it is possible to readily choose a strain wherein homologous recombination is caused. Furthermore, it is also possible to introduce a target gene by means of homologous recombination in such a manner that a gene wherein a gene that is lethal on a particular condition is linked with a drug resistance gene is inserted into a genome by means of homologous recombination in a method as described above and subsequently the drug resistance gene and the gene that is lethal on a particular condition are replaced thereby.

Moreover, a method that selects a recombinant microbe with an introduced target gene is not particularly limited, and it is preferable to be based on a technique that is capable of readily selecting only a recombinant microbe with an introduced target gene.

(A culturing method and an acquisition method for obtained 1,4-butanediol)

For example, a reaction in the present invention is most conveniently achieved in such a manner that a transformed body is cultured in a nutritive medium such as an LB medium at a temperature of 15° C.-40° C., desirably 18° C.-37° C. for about 24 hours, subsequently implanted to a medium with a normal carbon source, for example, a carbon source that is 0.01-50%, desirably 0.1-30%, of glucose, and continuously cultured at a similar temperature for about 1 hour-200 hours, wherein 1,4-butanediol is stored in a culture solution in such a process. Furthermore, a carbon source may be added continuously or intermittently depending on consumption of a carbon source that is caused by proliferation of a bacteria or proceeding of a reaction, and in such a case, a concentration of a carbon source in a reaction fluid is not limited to one described previously.

As a medium carbon source for culturing a microbe, it is possible to use, for example, a saccharide such as glucose, sucrose, or fructose, a polyol such as glycerol, an organic substance such as ethanol, acetic acid, citric acid, succinic acid, lactic acid, benzoic acid, or a fatty acid, or an alkali metal salt thereof, an aliphatic hydrocarbon such as an n-paraffin, an aromatic hydrocarbon, or a natural organic substance such as peptone, meat extract, fish extract, soybean flour, or bran, singly or in combination thereof, at a concentration of normally 0.01%-30%, desirably about 0.1%-20%.

For a medium nitrogen source for culturing a microbe, it is possible to use, for example, an inorganic nitrogen compound such as ammonium sulfate, ammonium phosphate, sodium nitrate, or potassium nitrate, a nitrogen-containing organic substance such as urea or uric acid, or a natural organic substance such as peptone, meat extract, fish extract, or soybean flour, singly or in combination thereof, at a concentration of normally 0.01%-20%, desirably about 0.1%-10%.

Moreover, it is possible to add a phosphate such as potassium dihydrogen phosphate, or a metal salt such as magnesium sulfate, ferrous sulfate, calcium acetate, manganese chloride, copper sulfate, zinc sulfate, cobalt sulfate, or nickel sulfate, as necessary, for growth of a bacteria or improvement of an enzyme activity. A concentration for addition thereof is different depending on a culturing condition, and normally, is 0.01%-5% for a phosphate, 10 ppm-1% for a magnesium salt, or about 0.1 ppm-1,000 ppm for other compounds. Furthermore, for a supply source of a vitamin, an amino acid, a nucleic acid, or the like, it is possible to add, for example, about 1 ppm-100 ppm of yeast extract, casamino acid, or a yeast nucleic acid, depending on a selected medium, for growth of a bacteria or improvement of an enzyme activity.

It is desirable to adjust a pH of a medium to 4.5-9, desirably 5-8. Furthermore, it is useful to fractionate from a culture solution by a method such as centrifugation or membrane filtration, and again suspend and react in water that contains a reaction raw material, physiological saline, a buffer that has a pH adjusted to be comparable to a pH for culturing and composed of phosphoric acid, acetic acid, boric acid, tris(hydroxymethyl)aminomethane, or the like, or a salt thereof, or the like, a microbial or bacterial body that is preliminarily cultured in a medium as described previously, in order to reduce an impurity in a reaction fluid and simplify subsequent fractionation of a product. Although a pH during a reaction is normally capable of being retained in a case where a buffer with a sufficient concentration is used, it is desirable to be execute appropriate adjustment by using sodium hydroxide, ammonia, or the like so as to provide a similar pH in a case where deviation from a pH as described above is caused by proceeding of a reaction.

In a case where 1,4-butanediol is stored in a reaction fluid and a reaction rate is lowered thereby, a method is preferable that adds water, physiological saline, a reaction buffer, or the like, into such a reaction fluid depending on a concentration of a product to execute continuous dilution thereof. Furthermore, at a point of time when a reaction rate is lowered, a bacteria is fractionated and a supernatant is recovered as a product solution and a fractionated bacteria is again returned to a solution or suspension that contains a reaction raw material, so that it is possible to recover such a reaction rate. It is possible to execute such an operation continuously or even batch-wise by using a centrifuge, a separation film, or the like.

It is possible to execute separation, recovery, and purification of 1,4-butanediol produced in a reaction fluid by using separation, recovery, and purification means for a general organic compound, after a bacterial body is eliminated from such a reaction fluid by means of centrifugation at a point of time when an amount of produced 1,4-butanediol reaches a substantial amount, or for such a reaction fluid directly. For example, extraction from a filtrate provided in such a manner that a bacterial body and others are eliminated from a culture solution is executed by using an appropriate organic solvent. 1,4-butanediol is obtained at a high purity by directly executing distillation for such an extract, as well as, further executing extraction with an appropriate solvent again, executing purification that uses chromatography on silica gel or the like, or applying multistep distillation or the like thereto.

(Practical Examples and Comparative Examples)

Next, the present invention will be described in more detail by describing practical examples.

Table 1 illustrates a summary of an envisaged reaction process, an enzyme that catalyzes each reaction process, and a gene that codes such an enzyme in Practical Examples 1 to 3 and Comparative Example 1. Here, a sequence number for a gene corresponds to a sequence number in a sequence listing.

TABLE 1

| Reaction process | Enzyme that catalyzes corresponding reaction |
|---|---|
| (1) Process that converts acetyl-CoA into acetoacetyl-CoA | β-ketothiolase, acetyl-CoA acetyl transferase, acetoacetyl-CoA synthase (EC number: 2.3.1.9) |
| (2) Process that converts acetoacetyl-CoA into 3-hydroxybutyryl-CoA | 3-hydroxybutyryl-CoA dehydrogenase (EC number: 1.1.1.35), acetoacetyl-CoA reductase (EC number: 1.1.1.36), 3-hydroxyacyl-CoA dehydrogenase (EC number: 1.1.1.157) |
| (3) Process that converts 3-hydroxybutyryl-CoA into crotonyl-CoA | enoyl-CoA hydratase (EC number: 4.2.1.17, EC number 4.2.1.119), 3-hydroxybutyryl-CoA dehydratase (EC number: 4.2.1.55) |
| (4) Process that converts crotonyl-CoA into 4-hydroxybutyryl-CoA | vinylacetyl-CoA delta-isomerase (EC number: 5.3.3.3) + 4-hydroxybutyryl-CoA dehydratase (EC number: 4.2.1.120) |
| (5) Process that converts 4-hydroxybutyryl-CoA into 1,4-butanediol | acyl-CoA reductase (EC number: 1.2.1.10) |

| | Used gene Practical Examples 1-3 and Comparative Example 1 | |
|---|---|---|
| Reaction process | Practical Example gene | Derivation |
| (1) Process that converts acetyl-CoA into acetoacetyl-CoA | Sequence number 2 | Provided by inventors (artificial synthesis) |
| (2) Process that converts acetoacetyl-CoA into 3-hydroxybutyryl-CoA | Sequence number 4 | Provided by inventors (artificial synthesis) |
| (3) Process that converts 3-hydroxybutyryl-CoA into crotonyl-CoA | Sequence number 6 | Provided by inventors (artificial synthesis) |
| (4) Process that converts crotonyl-CoA into 4-hydroxybutyryl-CoA | Sequence number 1 | Provided by inventors (artificial synthesis) |
| (5) Process that converts 4-hydroxybutyryl-CoA into 1,4-butanediol | Sequence number 8 | Provided by inventors (artificial synthesis) |

TABLE 1-continued

Used gene
Practical Examples 1-3 and
Comparative Example 1

| Reaction process | Comparative control gene | Derivation |
|---|---|---|
| (1) Process that converts acetyl-CoA into acetoacetyl-CoA | Sequence number 10 | thiL (*Clostridium acetobutylicum* ATCC 824-derived sequence, artificial synthesis) |
| (2) Process that converts acetoacetyl-CoA into 3-hydroxybutyryl-CoA | Sequence number 12 | hbd (*Clostridium acetobutylicum* ATCC 824-derived sequence, artificial synthesis) |
| (3) Process that converts 3-hydroxybutyryl-CoA into crotonyl-CoA | Sequence number 14 | crt (*Clostridium acetobutylicum* ATCC 824-derived sequence, artificial synthesis) |
| (4) Process that converts crotonyl-CoA into 4-hydroxybutyryl-CoA | Sequence number 16 | abfD (*Clostridium aminobutylicum* DSM 2634-derived sequence, artificial synthesis) |
| (5) Process that converts 4-hydroxybutyryl-CoA into 1,4-butanediol | Sequence number 17 | ald (*Clostridium beijerinckii* strain NRRL B592-derived sequence, artificial synthesis) |

COMPARATIVE EXAMPLE 1

A blunt end fragment was prepared by an ordinary method in such a manner that sequences that corresponded to 15 base pairs at an upstream side and a downstream side that contained CAT at an upstream side and ATG at a downstream side of a NdeI site among multi-cloning sites of expression vector pET17b (produced by Novagen, Inc.), respectively, were added to a 5'-end side and a 3'-end side upstream and downstream a gene sequence indicated by sequence number 10, respectively. Ligation of this fragment and a fragment provided by NdeI-treating pET17b (produced by Novagen, Inc.) was executed by In-Fusion HD Cloning Kit (produced by TAKARA BIO INC.) to obtain plasmid pETBD10.

A gene sequence indicated by sequence number 12 was inserted into an NdeI site of pET17b as a target by a method similar to that for pETBD10 to obtain plasmid pETBD12 that contained sequence 12.

An EcoRI site positioned downstream a termination codon of sequence 10 of pETBD10 and derived from multi-cloning sites of pET17b was cleaved by a restriction enzyme treatment to prepare a ring-opened fragment of pETBD10. Then, a fragment was prepared by means of PCR such that sequences that corresponded to 15 bp at an upstream side and 15 bp at a downstream side that contained an EcoRI site of pETBD10 described previously were added upstream and downstream a region of sequence 12 of pETBD12 and a region that contained T7 promoter derived from pET17b upstream thereof. Ligation of two obtained fragments was executed by In-Fusion HD Cloning Kit to obtain plasmid pETBD10-12 that contained sequences 10 and 12.

Subsequently, sequence numbers 14, 16, and 17 were sequentially added to a sequence downstream sequence 12 of pETBD10-12 as a further target in a similar manner to obtain plasmid pETBD10-12-14-16-17. Here, for addition of a sequence, ring-opening of a plasmid to be subjected to insertion was executed by cleavage with a restriction enzyme in a case where such a suitable restriction enzyme site that did not cleave a sequence subjected to insertion was present on a vector, or inverse PCR from a target site for insertion in a case where such a site was absent (similarly below). *Escherichia coli* JM109 (DE3) strain was transformed with pETBD10-12-14-16-17 to obtain *Escherichia coli* pETBD10-12-14-16-17/JM109 (DE3).

PRACTICAL EXAMPLES 1 to 3

A transformed body of JM109 (DE3) was obtained by a method similar to that of Comparative Example 1 in such a manner that transformation was executed with a plasmid provided in such a manner that respective genes of sequence numbers 10, 12, 14, 16, and 17 on plasmid pETBD10-12-14-16-17 were partially substituted by genes of sequence numbers 2, 4, 6, 1, and 8 that coded enzymes corresponding to enzymes that catalyzed respective processes.

Table 2 illustrates a summary of an envisaged reaction process, an enzyme that catalyzes each reaction process, and a gene that codes such an enzyme in Practical Examples 1 to 3 and Comparative Example 1. Here, a sequence number for a gene corresponds to a sequence number in a sequence listing.

TABLE 2

| Reaction process | Enzyme that catalyzes corresponding reaction |
|---|---|
| (1) Process that converts acetyl-CoA into acetoacetyl-CoA | β-ketothiolase, acetyl-CoA acetyl transferase, acetoacetyl-CoA synthase (EC number: 2.3.1.9) |
| (2) Process that converts acetoacetyl-CoA into 3-hydroxybutyryl-CoA | 3-hydroxybutyryl-CoA dehydrogenase (EC number: 1.1.1.35), acetoacetyl-CoA reductase (EC number: 1.1.1.36), 3-hydroxyacyl-CoA dehydrogenase (EC number: 1.1.1.157) |
| (3) Process that converts 3-hydroxybutyryl-CoA into crotonyl-CoA | enoyl-CoA hydratase (EC number: 4.2.1.17, EC number 4.2.1.119), 3-hydroxybutyryl-CoA dehydratase (EC number: 4.2.1.55) |
| (4) Process that converts crotonyl-CoA into 4-hydroxybutyryl-CoA | vinylacetyl-CoA delta-isomerase (EC number: 5.3.3.3) + 4-hydroxybutyryl-CoA dehydratase (EC number: 4.2.1.120) |
| (5) Process that converts 4-hydroxybutyryl-CoA into 1,4-butanediol | acyl-CoA reductase (EC number: 1.2.1.10) |
| Amount of produced 1,4-butanediol (mg/L) | |

| | Used gene (sequence number) | |
|---|---|---|
| Reaction process | Comparative Example 1 | Practical Example 1 |
| (1) Process that converts acetyl-CoA into acetoacetyl-CoA | 10 | 10 |
| (2) Process that converts acetoacetyl-CoA into 3-hydroxybutyryl-CoA | 12 | 4 |
| (3) Process that converts 3-hydroxybutyryl-CoA into crotonyl-CoA | 14 | 14 |
| (4) Process that converts crotonyl-CoA into 4-hydroxybutyryl-CoA | 16 | 1 |
| (5) Process that converts 4-hydroxybutyryl-CoA into 1,4-butanediol | 17 | 17 |
| Amount of produced 1,4-butanediol (mg/L) | n.d. | 24 |

TABLE 2-continued

| | Used gene (sequence number) | |
|---|---|---|
| Reaction process | Practical Example 2 | Practical Example 3 |
| (1) Process that converts acetyl-CoA into acetoacetyl-CoA | 10 | 2 |
| (2) Process that converts acetoacetyl-CoA into 3-hydroxybutyryl-CoA | 4 | 4 |
| (3) Process that converts 3-hydroxybutyryl-CoA into crotonyl-CoA | 14 | 6 |
| (4) Process that converts crotonyl-CoA into 4-hydroxybutyryl-CoA | 1 | 1 |
| (5) Process that converts 4-hydroxybutyryl-CoA into 1,4-butanediol | 8 | 8 |
| Amount of produced 1,4-butanediol (mg/L) | 72 | 240 |

COMPARATIVE EXAMPLE 2

Similarly to Practical Examples 1-3 and Comparative Example 1, plasmid pETBD11-13-15-16-18 was first prepared that contained gene sequences indicated by sequence numbers 11, 13, 15, 16, and 18 and thereby, *Escherichia coli* JM109 (DE3) strain was transformed to obtain *Escherichia coli* pETBD11-13-15-16-18/JM109 (DE3).

PRACTICAL EXAMPLES 4 to 6

Moreover, a transformed body of JM109 (DE3) was obtained in such a manner that transformation was executed with a plasmid provided in such a manner that respective genes of sequence numbers 11, 13, 15, 16, and 18 on plasmid pETBD11-13-15-16-18 were partially substituted by genes of sequence numbers 3, 5, 7, 1, and 9 that coded enzymes corresponding to enzymes that catalyzed respective processes.

A transformed body obtained in each of the respective practical examples and comparative examples was aerobically cultured in 5 mL of an LB medium that contained 100 mg/L of ampicillin at 37° C. for 12 hours. 0.1 mL of a culture solution was implanted to 5 mL of an LB medium that contained 1% of glucose, 100 mg/L of ampicillin, and 0.2 mM of IPTG and aerobically cultured at 30° C. for 48 hours. A supernatant of a culture solution was subjected to high performance liquid chromatography (HPLC: column; Shodex SH-1011 (produced by Showa Denko K. K.), column temperature: 60° C., eluent: 25 mM sulfuric acid aqueous solution, flow rate: 0.6 mL/min, detection: differential refraction detector). Table 3 and Table 4 illustrate a relationship between a gene that composes a used plasmid for a transformed body and an amount of 1,4-butanediol produced in a culture solution.

TABLE 3

| Reaction process | Enzyme that catalyzes corresponding reaction |
|---|---|
| (1) Process that converts acetyl-CoA into acetoacetyl-CoA | β-ketothiolase, acetyl-CoA acetyl transferase, acetoacetyl-CoA synthase (EC number: 2.3.1.9) |
| (2) Process that converts acetoacetyl-CoA into 3-hydroxybutyryl-CoA | 3-hydroxybutyryl-CoA dehydrogenase (EC number: 1.1.1.35), acetoacetyl-CoA reductase (EC number: 1.1.1.36), 3-hydroxyacyl-CoA dehydrogenase (EC number: 1.1.1.157) |
| (3) Process that converts 3-hydroxybutyryl-CoA into crotonyl-CoA | enoyl-CoA hydratase (EC number: 4.2.1.17, EC number 4.2.1.119), 3-hydroxybutyryl-CoA dehydratase (EC number: 4.2.1.55) |
| (4) Process that converts crotonyl-CoA into 4-hydroxybutyryl-CoA | vinylacetyl-CoA delta-isomerase (EC number: 5.3.3.3) + 4-hydroxybutyryl-CoA dehydratase (EC number: 4.2.1.120) |
| (5) Process that converts 4-hydroxybutyryl-CoA into 1,4-butanediol | acyl-CoA reductase (EC number: 1.2.1.10) |

| | Used gene Practical Examples 4-6 and Comparative Example 2 | |
|---|---|---|
| Reaction process | Practical Example gene | Derivation |
| (1) Process that converts acetyl-CoA into acetoacetyl-CoA | Sequence number 3 | Provided by inventors (artificial synthesis) |
| (2) Process that converts acetoacetyl-CoA into 3-hydroxybutyryl-CoA | Sequence number 5 | Provided by inventors (artificial synthesis) |
| (3) Process that converts 3-hydroxybutyryl-CoA into crotonyl-CoA | Sequence number 7 | Provided by inventors (artificial synthesis) |
| (4) Process that converts crotonyl-CoA into 4-hydroxybutyryl-CoA | Sequence number 1 | Provided by inventors (artificial synthesis) |
| (5) Process that converts 4-hydroxybutyryl-CoA into 1,4-butanediol | Sequence number 9 | Provided by inventors (artificial synthesis) |

| | Used gene Practical Examples 4-6 and Comparative Example 2 | |
|---|---|---|
| Reaction process | Comparative control gene | Derivation |
| (1) Process that converts acetyl-CoA into acetoacetyl-CoA | Sequence number 11 | PhaA (*Ralstonia eutropha* H16-derived, artificial synthesis) |
| (2) Process that converts acetoacetyl-CoA into 3-hydroxybutyryl-CoA | Sequence number 13 | PhaB (*Ralstonia eutropha* H16-derived, artificial synthesis) |
| (3) Process that converts 3-hydroxybutyryl-CoA into crotonyl-CoA | Sequence number 15 | phaJ (*Aeromonas caviae*-derived sequence, artificial synthesis) |
| (4) Process that converts crotonyl-CoA into 4-hydroxybutyryl-CoA | Sequence number 16 | abfD (*Clostridium aminobutylicum* DSM 2634-derived sequence, artificial synthesis) |
| (5) Process that converts 4-hydroxybutyryl-CoA into 1,4-butanediol | Sequence number 18 | adhE2 (*Clostridium acetobutylicum* ATCC 824-derived sequence, artificial synthesis) |

TABLE 4

| Reaction process | Enzyme that catalyzes corresponding reaction |
|---|---|
| (1) Process that converts acetyl-CoA into acetoacetyl-CoA | β-ketothiolase, acetyl-CoA acetyl transferase, acetoacetyl-CoA synthase (EC number: 2.3.1.9) |

TABLE 4-continued

| Reaction process | |
|---|---|
| (2) Process that converts acetoacetyl-CoA into 3-hydroxybutyryl-CoA | 3-hydroxybutyryl-CoA dehydrogenase (EC number: 1.1.1.35), acetoacetyl-CoA reductase (EC number: 1.1.1.36), 3-hydroxyacyl-CoA dehydrogenase (EC number: 1.1.1.157) |
| (3) Process that converts 3-hydroxybutyryl-CoA into crotonyl-CoA | enoyl-CoA hydratase (EC number: 4.2.1.17, EC number 4.2.1.119), 3-hydroxybutyryl-CoA dehydratase (EC number: 4.2.1.55), |
| (4) Process that converts crotonyl-CoA into 4-hydroxybutyryl-CoA | vinylacetyl-CoA delta-isomerase (EC number: 5.3.3.3) + 4-hydroxybutyryl-CoA dehydratase (EC number: 4.2.1.120) |
| (5) Process that converts 4-hydroxybutyryl-CoA into 1,4-butanediol | acyl-CoA reductase (EC number: 1.2.1.10) |

| Reaction process | Comparative Example 2 | Practical Example 4 |
|---|---|---|
| (1) Process that converts acetyl-CoA into acetoacetyl-CoA | 11 | 11 |
| (2) Process that converts acetoacetyl-CoA into 3-hydroxybutyryl-CoA | 13 | 13 |
| (3) Process that converts 3-hydroxybutyryl-CoA into crotonyl-CoA | 15 | 15 |
| (4) Process that converts crotonyl-CoA into 4-hydroxybutyryl-CoA | 16 | 1 |
| (5) Process that converts 4-hydroxybutyryl-CoA into 1,4-butanediol | 18 | 9 |
| Amount of produced 1,4-butanediol (mg/L) | n.d. | 35 |

TABLE 4-continued

| Reaction process | Practical Example 5 | Practical Example 6 |
|---|---|---|
| (1) Process that converts acetyl-CoA into acetoacetyl-CoA | 11 | 3 |
| (2) Process that converts acetoacetyl-CoA into 3-hydroxybutyryl-CoA | 13 | 5 |
| (3) Process that converts 3-hydroxybutyryl-CoA into crotonyl-CoA | 7 | 7 |
| (4) Process that converts crotonyl-CoA into 4-hydroxybutyryl-CoA | 1 | 1 |
| (5) Process that converts 4-hydroxybutyryl-CoA into 1,4-butanediol | 9 | 9 |
| Amount of produced 1,4-butanediol (mg/L) | 84 | 310 |

From Table 3 and Table 4, it is possible to obtain 1,4-butanediol at a high productivity by using a particular gene and a homolog thereof, in a manufacturing method for 1,4-butanediol that uses a microbe or a culture thereof, utilizes an enzyme reaction, and includes:

(1) a process that converts acetyl-CoA into acetoacetyl-CoA;

(2) a process that converts acetoacetyl-CoA into 3-hydroxybutyryl-CoA;

(3) a process that converts 3-hydroxybutyryl-CoA into crotonyl-CoA;

(4) a process that converts crotonyl-CoA into 4-hydroxybutyryl-CoA; and (5) a process that converts 4-hydroxybutyryl-CoA into 1,4-butanediol.

The present application claims priority based on Japanese Patent Application No. 2012-266501 filed on Dec. 5, 2012 before the Japan Patent Office and the entire contents of Japanese Patent Application No. 2012-266501 are incorporated by reference in the present application.

The invention claimed is:

1. A genetically modified microorganism that is capable of producing 1,4-butanediol, the microorganism being genetically modified to express:
    an enzyme that converts acetyl-CoA into acetoacetyl-CoA, the enzyme encoded by a nucleotide sequence having greater than or equal to 90% identity with respect to the nucleotide sequence of SEQ ID NO: 2 or SEQ ID NO: 3, in which one or more bases in the nucleotide sequence of SEQ ID NO: 2 or SEQ ID NO: 3 are deleted, substituted, or added,
    an enzyme that converts acetoacetyl-CoA into 3-hydroxybutyryl-CoA, the enzyme encoded by a nucleotide sequence having greater than or equal to 90% identity with respect to the nucleotide sequence of SEQ ID NO: 4 or SEQ ID NO: 5, in which one or more bases in the nucleotide sequence of SEQ ID NO: 4 or SEQ ID NO: 5 are deleted, substituted, or added,
    an enzyme that converts 3-hydroxybutyryl-CoA into crotonyl-CoA, the enzyme encoded by a nucleotide sequence having greater than or equal to 90% identity with respect to the nucleotide sequence of SEQ ID NO: 6 or SEQ ID NO: 7, in which one or more bases in the nucleotide sequence of SEQ ID NO: 6 or SEQ ID NO: 7 are deleted substituted or added,
    an enzyme that converts crotonyl-CoA into 4-hydroxybutyryl-CoA, the enzyme encoded by a nucleotide sequence having greater than or equal to 90% identity with respect to the nucleotide sequence of SEQ ID NO: 1, in which one or more bases in the nucleotide sequence of SEQ ID NO: 1 are deleted, substituted, or added, and
    an enzyme that converts 4-hydroxybutyryl-CoA into 1,4-butanediol, the enzyme encoded by a nucleotide sequence having greater than or equal to 90% identity with respect to the nucleotide sequence of SEQ ID NO: 8 or SEQ ID NO: 9, in which one or more bases in the nucleotide sequence of SEQ ID NO: 8 or SEQ ID NO: 9 are deleted, substituted, or added.

2. The genetically modified microorganism as claimed in claim 1, wherein at least one of the following applies:
    the nucleotide sequence encoding the enzyme that converts acetyl-CoA into acetoacetyl-CoA is SEQ ID NO: 2 or SEQ ID NO: 3;
    the nucleotide sequence encoding the enzyme that converts acetoacetyl-CoA into 3-hydroxybutyryl-CoA is SEQ ID NO: 4 or SEQ ID NO: 5;
    the nucleotide sequence encoding the enzyme that converts 3-hydroxybutyryl-CoA into crotonyl-CoA is SEQ ID NO: 6 or SEQ ID NO: 7;
    the nucleotide sequence encoding the enzyme that converts crotonyl-CoA into 4-hydroxybutyryl-CoA is SEQ ID NO: 1; and
    the nucleotide sequence encoding the enzyme that converts 4-hydroxybutyryl-CoA into 1,4-butanediol is SEQ ID NO: 8 or SEQ ID NO: 9.

3. A method of producing 1,4-butanediol comprising:
    culturing a genetically modified microorganism that produces 1,4-butanediol in a culture medium, and
    recovering the 1,4-butanediol from the culture medium,
    wherein the genetically modified microorganism expresses:
        an enzyme that converts acetyl-CoA into acetoacetyl-CoA, the enzyme encoded by a nucleotide sequence having greater than or equal to 90% identity with respect to the nucleotide sequence of SEQ ID NO: 2 or SEQ ID NO: 3, in which one or more bases in the nucleotide sequence of SEQ ID NO: 2 or SEQ ID NO: 3 are deleted, substituted, or added,
        an enzyme that converts acetoacetyl-CoA into 3-hydroxybutyryl-CoA, the enzyme encoded by a nucleotide sequence having greater than or equal to 90% identity with respect to the nucleotide sequence of SEQ ID NO: 4 or SEQ ID NO: 5, in which one or more bases in the nucleotide sequence of SEQ ID NO: 4 or SEQ ID NO: 5 are deleted, substituted, or added,
        an enzyme that converts 3-hydroxybutyryl-CoA into crotonyl-CoA, the enzyme encoded by a nucleotide sequence having greater than or equal to 90% identity with respect to the nucleotide sequence of SEQ ID NO: 6 or SEQ ID NO: 7, in which one or more bases in the nucleotide sequence of SEQ ID NO: 6 or SEQ ID NO: 7 are deleted, substituted, or added,
        an enzyme that converts crotonyl-CoA into 4-hydroxybutyryl-CoA, the enzyme encoded by a nucleotide sequence having greater than or equal to 90% identity with respect to the nucleotide sequence of SEQ ID NO: 1, in which one or more bases in the nucleotide sequence of SEQ ID NO: 1 are deleted, substituted, or added, and
        an enzyme that converts 4-hydroxybutyryl-CoA into 1,4-butanediol, the enzyme encoded by a nucleotide sequence having greater than or equal to 90% identity with respect to the nucleotide sequence of SEQ ID NO: 8 or SEQ ID NO: 9, in which one or more bases in the nucleotide sequence of SEQ ID NO: 8 or SEQ ID NO: 9 are deleted, substituted, or added.

4. The method according to claim 3, wherein at least one of the following applies:
- the nucleotide sequence encoding the enzyme that converts acetyl-CoA into acetoacetyl-CoA is SEQ ID NO: 2 or SEQ ID NO: 3;
- the nucleotide sequence encoding the enzyme that converts acetoacetyl-CoA into 3-hydroxybutyryl-CoA is SEQ ID NO: 4 or SEQ ID NO: 5;
- the nucleotide sequence encoding the enzyme that converts 3-hydroxybutyryl-CoA into crotonyl-CoA is SEQ ID NO: 6 or SEQ ID NO: 7;
- the nucleotide sequence encoding the enzyme that converts crotonyl-CoA into 4-hydroxybutyryl-CoA is SEQ ID NO: 1; and
- the nucleotide sequence encoding the enzyme that converts 4-hydroxybutyryl-CoA into 1,4-butanediol is SEQ ID NO: 8 or SEQ ID NO: 9.

* * * * *

SEQUENCE LISTING

<160> NUMBER OF SEQ ID NOS: 18

<210> SEQ ID NO 1
<211> LENGTH: 1473
<212> TYPE: DNA
<213> ORGANISM: Artificial Sequence
<220> FEATURE:
<223> OTHER INFORMATION: putative gene encoding enzyme converting
      crotonyl-CoA to 4-hydroxybutyryl-CoA

<400> SEQUENCE: 1

```
atgctgatga ccgccgaaca gtacatcgaa agcctgcgca agctgaacac gcgtgtctac      60
atgtttggtg aaaagatcga gaactgggta gaccatccca tgattcgccc ttcgatcaat     120
tgtgtggcaa tgacctatga actggcgcaa gatcccagt atgccgattt gatgaccacg      180
aaatcgaatc tgattggcaa gacgattaat cgcttcgcga acttacacca aagcaccgat     240
gatctgcgca agaaagtcaa aatgcaacgt ctgctgggcc agaaaaccgc gagttgcttt     300
cagcggtgtg ttgggatgga tgcgttcaat gccgtgtttt ccaccactta tgagattgat     360
cagaaatacg ggactaacta ccacaagaac ttcacggagt atctgaaata tattcaagaa     420
aatgacttga tcgtggatgg tgctatgacc gacccgaaag gcgaccgtgg gctggcaccg     480
```

```
agtgcccaga aagacccaga tctgtttctg cgcatcgtgg agaaacgcga ggatggtatc      540
gtagtccgtg gtgcgaaagc acatcaaacg ggctcaatta atagccatga gcacatcatt      600
atgccgacca ttgctatgac agaagcggat aaagactatg cggttagttt tgcttgtcca      660
tccgatgcgg atggtttgtt tatgatctat ggtcgccagt cttgcgacac ccgcaaaatg      720
gaggaaggcg cagatattga cttaggcaac aaacagtttg gcggccaaga agcccttgtc      780
gtgtttgaca acgtattcat cccgaatgat cgcattttct tatgccagga atacgatttt      840
gcgggaatga tggtcgaacg cttcgctggt tatcatcgcc agtcttacgg tggctgcaaa      900
gtgggtgtgg gtgacgtcgt tattggagcc gcagcccttg cagcggatta aacggtgcc       960 cagaaggcca gccatgtgaa agacaaactg atcgaaatga cacacttgaa cgaaaccctg      1020
tattgttgtg ggattgcgtg ctcagccgaa ggttatccga ctgcagccgg caattaccag      1080
atcgatctcc tccttgcgaa tgtgtgcaaa cagaacatta cgcgttttcc gtacgagatt      1140
gtacgtctgg cggaagatat tgccggagga ctgatggtta ctatgcctag cgaagcggac      1200
ttcaaaagcg aaacggttgt tgggcgtgat ggcgaaacca ttggcgattt ctgcaacaaa      1260
ttctttgcgg cagcaccgac ttgcaccaca gaagaacgga tgcgtgtgct ccgctttctg      1320
gagaacattt gtttaggcgc atccgctgtt gggtatcgta cagaatcgat gcatggtgcg      1380
ggctctccac aggctcaacg catcatgatt gcccgtcaag gcaatattaa cgcgaagaaa      1440
gaactcgcta aagcgatcgc tggcatcaaa taa                                  1473

<210> SEQ ID NO 2
<211> LENGTH: 1179
<212> TYPE: DNA
<213> ORGANISM: Artificial Sequence
<220> FEATURE:
<223> OTHER INFORMATION: putative gene encoding enzyme converting
      acetyl-CoA to acetoacetyl-CoA

<400> SEQUENCE: 2
atgcgtgatg tggtgatagt atcggcagta cggacagcaa taggcgcata cgggaagacg       60
cttaaggatg tcccggcaac ggagcttgga gcaattgtaa tcaaggaggc agtcagacga      120
gccaatatta accccaacga gattaacgag gttatttttcg gaaatgtgct tcaggccggc      180
ttgggacaga atcccgctcg ccaagctgcg gtaaaagcgg gtctgccact cgaaacgcct      240
gctttcacta ttaataaagt gtgtgggtct ggtctccgct caatttcgct agcagctcag      300
atcatcaagg caggggatgc tgatacgatt gtggttgggg gaatggaaaa catgtcccgg      360
tccccttatt tgatcaataa tcaacgctgg gggcagcgca tggggggactc ggagttagtc      420 gacgaaatga ttaaggacgg cctgtgggat gcgttcaatg gctatcatat gggtgtgaca      480
gctgaaaaca tcgctgagca atggaatatt acgcgtgagg aacaggatga attctcatta      540
atgagtcaac agaaagcaga aaagcgatc aagaacggcg aatttaaaga tgaaatcgtt      600
ccagtgctga tcaaaactaa aaaaggcgaa atcgtctttg accaggacga atttccgcgt      660
tttggcaaca ctattgaagc gttacgtaaa ctgaaaccga ttttaaaga aaatggtacc      720 gtcaccgccg gtaacgcgag cggcctcaat gatggtgcag cggcgttagt gattatgagc      780
gcggataaag ccaatgcgct gggtattaaa ccgttggcca aaattacctc ttacggcagc      840
tatggtgttg atccgagtat tatgggttac ggcgcctttt atgccaccaa agcggcgctg      900
gacaaaatca acctcaaacc ggaagatttg gacctgatcg aagccaacga agcgtacgcc      960
tcccaaagca ttgccgttac ccgcgatctg aacctggata tgtctaaagt taacgtgaac     1020
```

| | |
|---|---:|
| ggcggcgcca ttgcgctggg tcacccgatc ggcgccagtg gtgcccgcat cctggttacc | 1080 |
| ctgctgtatg cgatgcagaa acgtgacagc aaaaaaggcc tggcgaccct gtgcatcggt | 1140 |
| ggcggtcagg gcaccgcgct ggtcgtggaa cgtgattaa | 1179 |

<210> SEQ ID NO 3
<211> LENGTH: 1182
<212> TYPE: DNA
<213> ORGANISM: Artificial Sequence
<220> FEATURE:
<223> OTHER INFORMATION: putative gene encoding enzyme converting acetyl-CoA to acetoacetyl-CoA

<400> SEQUENCE: 3

| | |
|---|---:|
| atgaccgatg tcgtgattgt cagcgctgcg cggactgctg tagggaagtt tggtggttct | 60 |
| ctggcgaaaa ttccagctcc tgaactgggc gctgtggtaa tcaaagcggc actggaacgt | 120 |
| gcgggtgtca aaccggaaca ggtgtcggag gtcattatgg gtcaagtcct cactgcaggc | 180 |
| tccgccaaa accctgcacg ccaggctgcc attaaggcgg gtttgccggc catggtgcca | 240 |
| gcgatgacca tcaacaaggt atgcgggagt ggactgaaag cggtaatgct ggccgctaat | 300 |
| gcaattatgg ccggagatgc cgaaattgtt gtggcaggcg gtcaggagaa tatgtcggct | 360 |
| gcaccccatg tgcttccagg tagtcgtgac ggttttcgca tgggcgatgc taaactggtg | 420 |
| gataccatga tcgtcgatgg cctttgggat gtctacaacc agtatcacat gggcattacg | 480 |
| gccgaaaatg tggcaaaaga gtacggcatt actcgggaag cacaggatga attcgcagta | 540 |
| ggctcccaga cacaaagcaga agcggcgcag aaagcgggta attcgacga agaaatcgtg | 600 |
| ccggtgctca tcccgcaacg caaaggcgat ccggttgctt tcaaaaccga cgaatttgtt | 660 |
| cgccaaggcg caaccctgga cagcatgagc ggtctgaaac cggcatttga caaagccggc | 720 |
| acagttacgg ccgccaatgc cagcggtctg aacgatggtg cggcggccgt tgtggtcatg | 780 |
| tctgccgcga aagccaaaga gttaggcctg acacccttag cgacgatcaa gtcctatgcg | 840 |
| aatgcaggcg ttgacccgaa agtgatgggt atgggaccgg ttcctgcgag taaacgtgct | 900 |
| ctgtcacgtg ccgaatggac cccgcaagat ctggacttaa tggagatcaa cgaggcgttt | 960 |
| gcggcccagg cacttgccgt tcatcagcag atggggtggg atacgtcgaa agtgaacgtg | 1020 |
| aatggtggag ccattgcgat tgggcatccg attgggcgt cagggtgtcg catcttggtt | 1080 |
| accttgctgc acgaaatgaa acgtcgcgat gcgaagaaag gactcgcgag cctgtgcatt | 1140 |
| ggcggtggca tgggcgttgc gttagccgta gaacgcaagt aa | 1182 |

<210> SEQ ID NO 4
<211> LENGTH: 849
<212> TYPE: DNA
<213> ORGANISM: Artificial Sequence
<220> FEATURE:
<223> OTHER INFORMATION: putative gene encoding enzyme converting acetoacetyl-CoA to 3-hydroxybutyryl-CoA

<400> SEQUENCE: 4

| | |
|---|---:|
| atgaagaaag tgtgcgtaat cggagcaggc acaatgggat ctggtattgc gcaagcgttt | 60 |
| gctgccaaag gctttgaggt cgtattacgg gatatcaaag acgagttcgt agatcgtggg | 120 |
| ctggacttca tcaacaagaa tctcagcaaa ctcgttaaga agggcaaaat cgaagaagct | 180 |
| accaaagtgg agatcttaac ccgtatttcg ggtacggtgg acctgaacat ggcggcagat | 240 |
| tgcgatctgg ttatcgaagc ggcagttgag cgcatggaca tcaagaaaca gatctttgcg | 300 |

| | |
|---|---|
| gatttggaca acatttgtaa accggaaacg attctggcat ctaacactag ttccctgagc | 360 |
| attaccgaag ttgcgagcgc tacgaaacgt ccggataaag tgattggtat gcacttcttc | 420 |
| aaccctgcac cggtcatgaa actggtggaa gtaattcgcg ggattgccac atcacaggaa | 480 |
| acctttgatg ccgtcaaaga aacctcaatt gcgattggca agatcccgt ggaagttgct | 540 |
| gaggccccag gctttgtggt caatcgcatt ctgattccga tgatcaatga agcggttggc | 600 |
| atcctggccg aaggcattgc aagtgtggag gacattgata agcgatgaa actgggtgcc | 660 |
| aatcatccaa tgggtccgtt agaattgggt gatttcattg gccttgatat ttgtctggcg | 720 |
| atcatggatg tgctgtattc cgaaactggg gatagcaaat atcgccctca taccttgctg | 780 |
| aagaaatatg tccgtgccgg ttggcttggt cgcaaatcgg gaaaaggctt ttacgactac | 840 |
| tcgaaataa | 849 |

<210> SEQ ID NO 5
<211> LENGTH: 741
<212> TYPE: DNA
<213> ORGANISM: Artificial Sequence
<220> FEATURE:
<223> OTHER INFORMATION: putative gene encoding enzyme converting
      acetoacetyl-CoA to 3-hydroxybutyryl-CoA

<400> SEQUENCE: 5

| | |
|---|---|
| atgacacaac gcattgcgta tgtcacaggc ggtatgggtg gcattggcac cgccatttgc | 60 |
| cagcgtttag ccaaagatgg cttcgcgtg gtagcaggat gtggtccgaa cagtccacgt | 120 |
| cgcgaaaagt ggctgaaaca gcagaaagcc cttggcttcg atttcatcgc tagcgaaggt | 180 |
| aacgtagcgg attgggatag cacgaaaacg gcgtttgaca aggtcaaatc tgaggtaggc | 240 |
| gaagttgacg tgctgatcaa caatgctggt atcacccgtg atgtggtgtt tcggaaaatg | 300 |
| actcgtgccg attgggatgc agtgatcgac accaatctca cttcgctgtt caacgttacg | 360 |
| aaacaggtga ttgacggcat ggctgatcgc ggttggggtc gtatcgtcaa catttcctcg | 420 |
| gttaatgggc agaaaggtca gtttgggcag accaactatt ccacggcgaa agcagggctg | 480 |
| catggcttta cgatggcgtt agcccaagaa gtggcgacca aggagttac cgtcaatacc | 540 |
| gtgagtccgg gctacattgc gaccgatatg gttaaagcga ttcgccaaga cgttctggac | 600 |
| aagatcgtgg caacaattcc ggtcaaacgc ttggggttgc ctgaagagat tgcctcaatc | 660 |
| tgcgcttggc tgtcatctga ggaaagcggc ttttcgactg gtgcagattt cagcctgaat | 720 |
| ggaggcctgc acatgggtta a | 741 |

<210> SEQ ID NO 6
<211> LENGTH: 786
<212> TYPE: DNA
<213> ORGANISM: Artificial Sequence
<220> FEATURE:
<223> OTHER INFORMATION: putative gene encoding enzyme converting
      3-hydroxybutyryl-CoA to crotonyl-CoA

<400> SEQUENCE: 6

| | |
|---|---|
| atggaactga caatgtgat tctggaaaag gagggtaaag ttgcggtggt taccatcaac | 60 |
| cgtcccaaag cgctgaatgc ccttaatagc gatacgctga agagatgga ctatgtgatc | 120 |
| ggcgaaatcg aaaacgactc tgaagtctta gctgtcattc tgaccggtgc tggagagaaa | 180 |
| agctttgtag cgggagcgga catcagcgaa atgaaagaaa tgaacacgat tgaaggacgc | 240 |
| aaattcggca ttttggcaa caaggtgttt cgtcgcctgg aactgctgga gaaccggta | 300 |
| attgcagccg tcaatggctt tgcgttgggt ggtggttgtg agatcgcaat gtcgtgtgac | 360 |

| | | |
|---|---|---|
| attcgcattg catcttccaa cgctcgtttt ggccaaccgg aagtaggcct cggtattacc | | 420 |
| cctgggtttg gcggcactca acggttaagt cgcttagtgg ggatgggtat ggcgaaacag | | 480 |
| ctgattttca cagcgcagaa catcaaagcc gatgaagcat tgcgtattgg ccttgtcaac | | 540 |
| aaagtggttg aaccgagtga actgatgaat accgcgaaag aaatcgcgaa taagatcgtt | | 600 |
| agcaatgccc cagttgccgt gaaactctcg aaacaggcca ttaaccgtgg catgcagtgc | | 660 |
| gatatcgata ctgcactggc cttcgaatca gaggcatttg gggaatgctt ttccaccgaa | | 720 |
| gatcagaagg atgcgatgac ggctttcatt gagaaacgca aaattgaggg tttcaagaat | | 780 |
| cgctaa | | 786 |

<210> SEQ ID NO 7
<211> LENGTH: 405
<212> TYPE: DNA
<213> ORGANISM: Artificial Sequence
<220> FEATURE:
<223> OTHER INFORMATION: putative gene encoding enzyme converting
      3-hydroxybutyryl-CoA to crotonyl-CoA

<400> SEQUENCE: 7

| | | |
|---|---|---|
| atgagtgcac agagccttga agttggccag aaagcgcgtt tgtcgaaacg ctttggtgca | | 60 |
| gcggaagtag cggcgtttgc cgcgctgtct gaggacttca accctctgca ccttgatccg | | 120 |
| gcctttgcag ctaccactgc ctttgaacgt cccattgtgc atgggatgct gctggctagc | | 180 |
| ctgtttagcg gcttgctcgg ccaacagctg ccaggcaaag gctccatcta tctgggtcag | | 240 |
| tcactctcgt tcaaactgcc ggttttcgtc ggagatgagg ttaccgccga agtcgaagtg | | 300 |
| accgctttac gcgaggataa gccgattgcg acgctgacta cccgcatctt cacgcaaggt | | 360 |
| ggtgccttag cggtaacagg ggaagcagtg gtgaaactgc cgtaa | | 405 |

<210> SEQ ID NO 8
<211> LENGTH: 1407
<212> TYPE: DNA
<213> ORGANISM: Artificial Sequence
<220> FEATURE:
<223> OTHER INFORMATION: putative gene encoding enzyme converting
      4-hydroxybutyryl-CoA to 1,4-butanediol

<400> SEQUENCE: 8

| | | |
|---|---|---|
| atgaacaaag acactctgat cccgacgacc aaagacctga agtgaaaaac gaatggcgag | | 60 |
| aacattaacc tgaaaaacta caaagacaac agctcctgtt ttggcgtctt tgaaaacgta | | 120 |
| gagaacgcta tttcatcggc cgttcatgcg cagaagattt tgagcctcca ttatactaaa | | 180 |
| gaacaacgtg agaaaatcat caccgaaatt cgcaaagcag cgttacagaa caaagaagtt | | 240 |
| ttggccacta tgattctgga agaaacccac atgggccgtt atgaagataa atcctgaaa | | 300 |
| cacgaactgg tggcaaaata taccccctggt accgaagatc tgacgacaac agcgtggtca | | 360 |
| ggggataacg gcttaaccgt ggtggaaatg agtccgtatg gtgtgattgg tgcgattacc | | 420 |
| ccgtctacga atccgaccga aaccgtcatc tgcaatagca ttggcatgat tgcggcaggg | | 480 |
| aacgctgtcg tatttaacgg gcatccgtgt gcaaagaaat gcgttgcttt tgcggtagag | | 540 |
| atgatcaaca aagcaatcat ttcctgtgga ggccctgaaa acctggtcac aaccattaaa | | 600 |
| aacccaacga tggaaagcct ggatgcgatt atcaaacatc cctcgattaa actgctttgt | | 660 |
| gggactggtg gaccaggtat ggtgaaaacc ttactgaaca gtggcaagaa agcgattggc | | 720 |
| gcgggtgcgg gcaatccgcc tgtgattgtc gatgacacgg ccgatattga aaagctggt | | 780 |

| | |
|---|---|
| cgttcaatta tcgagggttg ctcgttcgac aacaacttgc cgtgcattgc tgagaaagaa | 840 |
| gttttcgtat tcgaaaatgt tgctgatgat ctcatcagca atatgctgaa aaacaatgcg | 900 |
| gttatcatta atgaggatca ggtttctaag ctgattgatc tggtgctgca gaaaaacaat | 960 |
| gagactcagg aatacttcat taataagaaa tgggttggca agatgccaa gttattcctc | 1020 |
| gatgagattg acgtggaaag tccgagcaat gtgaaatgca tcatttgtga agtcaacgcc | 1080 |
| aatcacccat ttgtgatgac cgaattgatg atgccgattc ttcccatcgt acgggtgaaa | 1140 |
| gacattgatg aagccattaa atacgccaaa attgccgaac aaaatcgcaa gcattccgca | 1200 |
| tatatctact cgaagaatat cgacaatctt aatcgcttcg aacgcgaaat cgatacgacg | 1260 |
| atctttgtca agaatgcgaa aagtttcgca ggagttggct atgaagcaga gggctttacg | 1320 |
| acctttacaa tcgccggtag caccggtgaa ggcatcactt ctgcgcgcaa ctttacccgt | 1380 |
| caacgccgtt gcgtgctggc cgggtaa | 1407 |

<210> SEQ ID NO 9
<211> LENGTH: 2577
<212> TYPE: DNA
<213> ORGANISM: Artificial Sequence
<220> FEATURE:
<223> OTHER INFORMATION: putative gene encoding enzyme converting
4-hydroxybutyryl-CoA to 1,4-butanediol

<400> SEQUENCE: 9

| | |
|---|---|
| atgaaagtga caaaccagaa agaactgaaa cagaaattga cgaacttcg cgaggcgcag | 60 |
| aaaaaatttg caacctacac gcaagaacag gtagacaaaa tcttcaaaca gtgcgcaatc | 120 |
| gcggcagcca agaacgcat taatctggcg aaattagccg ttgaggaaac tggtattgga | 180 |
| ctggtcgagg acaaaatcat taagaatcat ttcgccgcag aatacattta caacaaatac | 240 |
| aagaacgaga aacttgcgg cattatcgat cacgatgact cgctgggcat tacgaaagtc | 300 |
| gccgaaccta ttggcattgt agctgcgatc gttccgacaa cgaatcccac tagtaccgcc | 360 |
| atttttcaaaa gcctgattag tcttaagacc cgcaatgcca tttttctttc tccgcatccg | 420 |
| cgtgccaaga atctacgat cgcggcggct aaactgatct tggatgcggc cgttaaagca | 480 |
| ggcgcaccga agaacattat tgggtggatt gacgaaccat ctatcgaact ctcacaggac | 540 |
| ttgatgtcgg aagctgacat tatcctggca acaggcggac cgtcgatggt gaaagcagcg | 600 |
| tattcaagtg gtaaaccggc aattggtgtc ggtgctggca cacgccagc aatcatcgat | 660 |
| gagagcgcgg atattgatat ggctgtgtcg tctattatcc tcagcaaaac gtatgacaat | 720 |
| ggcgtgattt gcgcgtcgga acagtcgatt ctggttatga attccatcta tgaaaaggtg | 780 |
| aaagaagaat tcgtaaagcg cggctcctat atcctgaacc agaacgaaat tgccaaaatc | 840 |
| aaagaaacga tgttcaagaa tggggcgatc aatgcggata ttgtcggcaa atcagcctat | 900 |
| attatcgcga aaatggccgg cattgaagtt ccgcaaacca cgaaaattct gatcggcgag | 960 |
| gttcagtccg tagagaaatc cgaattatttt tcacatgaaa agctgagccc ggttctggct | 1020 |
| atgtacaaag tgaaagattt tgatgaagcc ttgaagaaag cccaacgtct tatcgaactt | 1080 |
| ggtgaagtg tcatacatc tagtctgtac attgatagcc aaaataacaa agataaggtc | 1140 |
| aaagaattg gtctggcaat gaaaaccagc cgtacattta tcaatatgcc atcaagtcaa | 1200 |
| ggtgccagtg gggacttgta taattttgcg attgctccct cctttactct gggctgtggc | 1260 |
| acctggggtg gcaactccgt gagccaaaat gtggaaccca acatttgct gaacatcaaa | 1320 |
| tcggtcgccg aacgccgcga aaatatgtta tggtttaagg tacctcagaa gatttacttt | 1380 |

```
aaatatggct gcctgcgttt cgcgctgaag gaactgaaag atatgaacaa aaaacgcgca      1440
tttatcgtga ccgacaaaga cctctttaaa ttagggtatg ttaacaaaat taccaaagtc      1500
ttagatgaga ttgacatcaa atacagcatt ttcaccgata ttaagtcgga ccctaccatt      1560
gatagcgtga agaaaggcgc caaagaaatg ctgaactttg aaccggatac cattatttca      1620
attggtggtg gttctcccat ggacgcagca aaagtgatgc atctcttgta tgaatacccg      1680
gaggccgaga ttgagaactt agctatcaac tttatggata ttcgcaaacg tatctgcaac      1740
ttcccgaagc tgggcaccaa agcgatctca gttgccattc caactacggc tggtaccggc      1800
agcgaggcta caccatttgc ggttatcacc aatgacgaaa ccggaatgaa atatcctctc      1860
acgagctatg agctgactcc gaatatggct attatcgaca ccgaattaat gctgaacatg      1920
ccgcggaaac tgaccgcggc aaccggtatt gatgcgcttg tccacgcgat cgaagcgtat      1980
gtaagcgtga tggccacgga ttatactgat gaactggcgc tgcgtgcaat caaaatgatt      2040
ttcaaatatc tgcctcgcgc gtacaaaaac gggactaatg atatcgaggc acgtgagaaa      2100
atggctcatg cctccaacat tgcgggtatg gcatttgcca atgctttcct gggtgtgtgt      2160
catagcatgg cgcacaaatt aggagccatg caccacgtgc cacacgggat tgcgtgtgcg      2220
gtcctcatcg aagaagtgat caaatataac gcaaccgatt gtccgacgaa acagacggcc      2280
tttccgcagt acaaatcgcc aaatgcgaag cgcaaatacg cagagattgc ggaatatttg      2340
aatctgaaag gcaccagcga taccgagaaa gttacggcgc tgattgaagc gatctctaag      2400
ctgaagatcg atctgagcat tccgcagaac attagtgctg ctgggattaa caaaaaagat      2460
ttctacaaca ccctggataa aatgagcgaa ctcgcgttcg atgatcaatg cacaaccgcc      2520
aatccgcggt atccgcttat ctctgaactg aaagacattt atatcaagtc ctttttaa        2577

<210> SEQ ID NO 10
<211> LENGTH: 1179
<212> TYPE: DNA
<213> ORGANISM: Artificial Sequence
<220> FEATURE:
<223> OTHER INFORMATION: Clostridium acetobutylicum thiL gene

<400> SEQUENCE: 10
atgagagatg tagtaatagt aagtgctgta agaactgcaa taggagcata tggaaaaaca        60
ttaaaggatg tacctgcaac agagttagga gctatagtaa taaggaagc tgtaagaaga       120 gctaatataa atccaaatga gattaatgaa gttattttg gaaatgtact tcaagctgga       180
ttaggccaaa acccagcaag acaagcagca gtaaaagcag gattaccttt agaaacacct       240
gcgtttacaa tcaataaggt ttgtggttca ggtttaagat ctataagttt agcagctcaa       300
attataaaag ctggagatgc tgataccatt gtagtaggtg gtatggaaaa tatgtctaga       360
tcaccatatt tgattaacaa tcagagatgg ggtcaaagaa tgggagatag tgaattagtt       420
gatgaaatga taaaggatgg tttgtgggat gcatttaatg gatatcatat gggagtaact       480
gcagaaaata ttgcagaaca atggaatata acaagagaag agcaagatga attttcactt       540
atgtcacaac aaaaagctga aaaagccatt aaaaatggag aatttaagga tgaaatagtt       600
cctgtattaa taaagactaa aaaaggtgaa atagtctttg atcaagatga atttcctaga       660
ttcggaaaca ctattgaagc attaagaaaa cttaaaccta ttttcaagga aatggtact       720 gttacagcag gtaatgcatc cggattaaat gatggagctg cagcactagt aataatgagc       780
gctgataaag ctacgctct cggaataaaa ccacttgcta agattacttc ttacggatca       840
tatggggtag atccatcaat aatgggatat ggagcttttt atgcaactaa agctgcctta       900
```

-continued

```
gataaaatta atttaaaacc tgaagactta gatttaattg aagctaacga ggcatatgct      960
tctcaaagta tagcagtaac tagagattta aatttagata tgagtaaagt taatgttaat     1020
ggtggagcta tagcacttgg acatccaata ggtgcatctg gtgcacgtat tttagtaaca     1080
ttactatacg ctatgcaaaa aagagattca aaaaaaggtc ttgctactct atgtattggt     1140
ggaggtcagg gaacagctct cgtagttgaa agagactaa                            1179
```

<210> SEQ ID NO 11
<211> LENGTH: 1182
<212> TYPE: DNA
<213> ORGANISM: Artificial Sequence
<220> FEATURE:
<223> OTHER INFORMATION: Ralstonia eutropha phaA gene

<400> SEQUENCE: 11

```
atgactgacg ttgtcatcgt atccgccgcc cgcaccgcgg tcggcaagtt tggcggctcg      60
ctggccaaga tcccggcacc ggaactgggt gccgtggtca tcaaggccgc gctggagcgc     120
gccggcgtca agccggagca ggtgagcgaa gtcatcatgg gccaggtgct gaccgccggt     180
tcgggccaga ccccgcacg ccaggccgcg atcaaggccg gctgccggc gatggtgccg     240 gccatgacca tcaacaaggt gtgcggctcg ggcctgaagg ccgtgatgct ggccgccaac     300
gcgatcatgg cgggcgacgc cgagatcgtg gtggccggcg gccaggaaaa catgagcgcc     360
gccccgcacg tgctgccggg ctcgcgcgat ggtttccgca tgggcgatgc caagctggtc     420
gacaccatga tcgtcgacgg cctgtgggac gtgtacaacc agtaccacat gggcatcacc     480
gccgagaacg tggccaagga atacggcatc acacgcgagg cgcaggatga gttcgccgtc     540
ggctcgcaga acaaggccga agccgcgcag aaggccggca gtttgacga agagatcgtc     600 ccggtgctga tcccgcagcg caagggcgac ccggtggcct tcaagaccga cgagttcgtg     660
cgccagggcg ccacgctgga cagcatgtcc ggcctcaagc ccgccttcga caaggccggc     720
acggtgaccg cggccaacgc ctcgggcctg aacgacggcg ccgccgcggt ggtggtgatg     780
tcggcggcca aggccaagga actgggcctg accccgctgg ccacgatcaa gagctatgcc     840
aacgccggtg tcgatcccaa ggtgatgggc atgggcccgg tgccggcctc caagcgcgcc     900
ctgtcgcgcg ccgagtggac cccgcaagac ctggacctga tggagatcaa cgaggccttt     960
gccgcgcagg cgctggcggt gcaccagcag atgggctggg acacctccaa ggtcaatgtg    1020
aacggcggcg ccatcgccat cggccacccg atcggcgcgt cgggctgccg tatcctggtg    1080
acgctgctgc acgagatgaa gcgccgtgac gcgaagaagg gcctggcctc gctgtgcatc    1140
ggcggcggca tgggcgtggc gctggcagtc gagcgcaaat aa                       1182
```

<210> SEQ ID NO 12
<211> LENGTH: 849
<212> TYPE: DNA
<213> ORGANISM: Artificial Sequence
<220> FEATURE:
<223> OTHER INFORMATION: Clostridium acetobutylicum hbd gene

<400> SEQUENCE: 12

```
atgaaaaagg tatgtgttat aggtgcaggt actatgggtt caggaattgc tcaggcattt     60
gcagctaaag gatttgaagt agtattaaga gatattaaag atgaatttgt tgatagagga    120
ttagattttt tcaataaaaa tcttctctaa ttagttaaaa aaggaaagat agaagaagct    180
actaaagttg aaatcttaac tagaatttcc ggaacagttg accttaatat ggcagctgat    240
```

```
tgcgatttag ttatagaagc agctgttgaa agaatggata ttaaaaagca gattttttgct    300 gacttagaca atatatgcaa gccagaaaca attcttgcat caaatacatc atcactttca    360
ataacagaag tggcatcagc aactaaaaga cctgataagg ttataggtat gcatttcttt    420
aatccagctc ctgttatgaa gcttgtagag gtaataagag gaatagctac atcacaagaa    480
acttttgatg cagttaaaga gacatctata gcaataggaa aagatcctgt agaagtagca    540
gaagcaccag gatttgttgt aaatagaata ttaataccaa tgattaatga agcagttggt    600
atattagcag aaggaatagc ttcagtagaa gacatagata aagctatgaa acttggagct    660
aatcacccaa tgggaccatt agaattaggt gattttatag gtcttgatat atgtcttgct    720
ataatggatg ttttatactc agaaactgga gattctaagt atagaccaca tacattactt    780
aagaagtatg taagagcagg atggcttgga agaaaatcag gaaaaggttt ctacgattat    840
tcaaaataa                                                          849

<210> SEQ ID NO 13
<211> LENGTH: 741
<212> TYPE: DNA
<213> ORGANISM: Artificial Sequence
<220> FEATURE:
<223> OTHER INFORMATION: Ralstonia eutropha phaB gene

<400> SEQUENCE: 13
atgactcagc gcattgcgta tgtgaccggc ggcatggggt gtatcggaac cgccatttgc     60
cagcggctgg ccaaggatgg cttccgtgtg gtggccggtt gcggccccaa ctcgccgcgc    120
cgcgaaaagt ggctggagca gcagaaggcc ctgggcttcg atttcattgc ctcggaaggc    180
aatgtggctg actgggactc gaccaagacc gcattcgaca aggtcaagtc cgaggtcggc    240
gaggttgatg tgctgatcaa caacgccggt atcacccgcg acgtggtgtt ccgcaagatg    300
acccgcgccg actgggatgc ggtgatcgac accaacctga cctcgctgtt caacgtcacc    360
aagcaggtga tcgacggcat ggccgaccgt ggctggggcc gcatcgtcaa catctcgtcg    420
gtgaacgggc agaagggcca gttcggccag accaactact ccaccgccaa ggccggcctg    480
catggcttca ccatggcact ggcgcaggaa gtggcgacca agggcgtgac cgtcaacacg    540
gtctctccgg gctatatcgc caccgacatg gtcaaggcga tccgccagga cgtgctcgac    600
aagatcgtcg cgacgatccc ggtcaagcgc ctgggcctgc cggaagagat cgcctcgatc    660
tgcgcctggt tgtcgtcgga ggagtccggt ttctcgaccg gcgccgactt ctcgctcaac    720
ggcggcctgc atatgggctg a                                             741

<210> SEQ ID NO 14
<211> LENGTH: 786
<212> TYPE: DNA
<213> ORGANISM: Artificial Sequence
<220> FEATURE:
<223> OTHER INFORMATION: Clostridium acetobutylicum crt gene

<400> SEQUENCE: 14
atggaactaa acaatgtcat ccttgaaaag gaaggtaaag ttgctgtagt taccattaac     60
agacctaaag cattaaatgc gttaaatagt gatacactaa agaaatggga ttatgttata    120
ggtgaaattg aaaatgatag cgaagtactt gcagtaattt aactggagc aggagaaaaa    180 tcatttgtag caggagcaga tatttctgag atgaaggaa tgaataccat gaaggtagaa    240
aaattcggga tacttggaaa taagtgtttt agaagattag aacttcttga aaagcctgta    300
atagcagctg ttaatggttt tgctttagga ggcggatgcg aaatagctat gtcttgtgat    360
```

```
ataagaatag cttcaagcaa cgcaagattt ggtcaaccag aagtaggtct cggaataaca      420
cctggttttg gtggtacaca aagactttca agattagttg gaatgggcat ggcaaagcag      480
cttatattta ctgcacaaaa tataaaggca gatgaagcat taagaatcgg acttgtaaat      540
aaggtagtag aacctagtga attaatgaat acagcaaaag aaattgcaaa caaaattgtg      600
agcaatgctc cagtagctgt taagttaagc aaacaggcta ttaatagagg aatgcagtgt      660
gatattgata ctgctttagc atttgaatca aagcatttg gagaatgctt ttcaacagag       720
gatcaaaagg atgcaatgac agctttcata gagaaaagaa aaattgaagg cttcaaaaat      780
agatag                                                                 786

<210> SEQ ID NO 15
<211> LENGTH: 405
<212> TYPE: DNA
<213> ORGANISM: Artificial Sequence
<220> FEATURE:
<223> OTHER INFORMATION: Aeromonas caviae phaJ gene

<400> SEQUENCE: 15
atgagcgcgc agagcctgga agtgggtcaa aaagctcgcc tgtccaaacg ttttggtgca       60
gcagaagttg cggccttcgc agcactgtct gaagacttca atccgctgca tctggacccg      120
gcattcgcgg caaccaccgc atttgaacgc ccgatcgttc atggtatgct gttggcaagc      180
ctgtttagcg gtctgctggg tcagcagctg ccgggcaaag gtagcattta cctgggtcag      240
agcctgagct ttaaactgcc ggtgttcgtc ggtgacgagg tcacggcgga ggtcgaggtt      300
acggccctgc gtgaggacaa gccgatcgcg accctgacca cccgtatttt cacccagggt      360
ggcgcgttgg ccgtgacggg tgaggccgtg gtcaaactgc cgtaa                     405

<210> SEQ ID NO 16
<211> LENGTH: 1473
<212> TYPE: DNA
<213> ORGANISM: Artificial Sequence
<220> FEATURE:
<223> OTHER INFORMATION: Clostridium aminobutylicum abfD gene

<400> SEQUENCE: 16
atgttaatga cagcagaaca gtacattgag agtctaagaa agctaaacac aagagtttat       60
atgtttggtg aaaaaatcga gaattgggtg gatcatccaa tgatcagacc ttccatcaac      120
tgcgtagcaa tgacttatga attagctcag gatcctcagt acgctgactt aatgactaca      180
aagtcaaact taataggtaa aactatcaac agatttgcaa atctacacca gagcacagat      240
gaccttagaa aaaaggttaa gatgcagaga cttcttggac agaagaccgc atcatgcttc      300
cagagatgtg taggtatgga cgctttcaat gcagttttct caactacata tgaaatcgac      360
cagaaatatg gaacaaacta tcacaagaac tttactgaat acttaaagta tatacaggaa      420
aatgacctta ttgttgacgg tgcaatgact gaccctaagg gtgacagagg acttgctcca      480
tccgcacaga aggatccaga tcttttcttg agaatcgttg aaaaaagaga gatggtatc       540 gttgtaagag gagctaaggc tcaccagact ggttccatca actcccacga acacatcatc      600
atgcctacaa tcgctatgac agaagctgat aaggattatg cagtatcatt tgcttgtcct      660
tccgatgctg atggtctatt catgatctac ggcagacagt catgtgacac aagaaagatg      720
gaagaaggcg ctgacattga ccttggtaac aagcagttcg gcggacagga agctttagtc      780
gtattcgata acgtatttat tccaaatgac agaatcttcc tttgccaaga atatgatttc      840
```

```
gctggcatga tggtagaaag atttgctgga taccacagac agtcatacgg cggatgtaag    900
gttggagtag gcgacgttgt aatcggtgct gctgctttag ctgctgacta caatggagct    960
cagaaggctt ctcacgttaa agataagctt atcgaaatga ctcacttaaa tgaaacttta   1020
tattgctgcg gtattgcttg ttcagcagaa ggttatccaa ctgctgctgg taactatcag   1080
attgaccttc ttcttgcaaa tgtatgtaag cagaacatca ctagattccc ttacgaaatc   1140
gtaagactag ctgaagatat cgctggtgga ttaatggtta ctatgccttc agaagctgac   1200
tttaagtcag aaacagttgt tggtagagat ggcgaaacta ttggagattt ctgcaataag   1260
ttcttcgctg ctgctcctac ttgcacaaca gaagaaagaa tgagagttct tagattctta   1320
gaaaacatct gcttaggtgc atccgctgta ggttacagaa ctgaatccat gcatggtgca   1380
ggttcccctc aggctcagag aatcatgatc gctcgtcagg gcaacatcaa cgctaagaaa   1440
gaattagcta aggcaatcgc tggaattaaa taa                                1473

<210> SEQ ID NO 17
<211> LENGTH: 1407
<212> TYPE: DNA
<213> ORGANISM: Artificial Sequence
<220> FEATURE:
<223> OTHER INFORMATION: Clostridium beijerinckii ald gene

<400> SEQUENCE: 17
atgaataaag acacactaat acctacaact aaagatttaa agtaaaaac aaatggtgaa     60 aacattaatt taaagaacta caaggataat tcttcatgtt tcggagtatt cgaaaatgtt    120
gaaaatgcta taagcagcgc tgtacacgca caaaagatat tatcccttca ttatacaaaa    180
gagcaaagag aaaaaatcat aactgagata gaaaggccg cattacaaaa taaagaggtc    240
ttggctacaa tgattctaga agaaacacat atgggaagat atgaggataa atattaaaa    300 catgaattgg tagctaaata tactcctggt acagaagatt taactactac tgcttggtca    360
ggtgataatg tcttacagt tgtagaaatg tctccatatg tgttataggt gcaataact    420 ccttctacga atccaactga aactgtaata tgtaatagca taggcatgat agctgctgga    480
aatgctgtag tatttaacgg acacccatgc gctaaaaaat gtgttgcctt tgctgttgaa    540
atgataaata aggcaattat ttcatgtggc ggtcctgaaa atctagtaac aactataaaa    600
aatccaacta tggagtctct agatgcaatt attaagcatc cttcaataaa acttcttttgc    660 ggaactgggg gtccaggaat ggtaaaaacc ctcttaaatt ctggtaagaa agctataggt    720
gctggtgctg gaaatccacc agttattgta gatgatactg ctgatataga aaaggctggt    780
aggagcatca ttgaaggctg ttctttttgat aataatttac cttgtattgc agaaaaagaa    840
gtatttgttt ttgagaatgt tgcagatgat ttaatatcta acatgctaaa aaataatgct    900
gtaattataa atgaagatca agtatcaaaa ttaatagatt tagtattaca aaaaaataat    960
gaaactcaag aatactttat aaacaaaaaa tgggtaggaa aagatgcaaa attattctta   1020
gatgaaatag atgttgagtc tccttcaaat gttaaatgca taatctgcga agtaaatgca   1080
aatcatccat ttgttatgac agaactcatg atgccaatat tgccaattgt aagagttaaa   1140
gatatagatg aagctattaa atatgcaaag atagcagaac aaaatagaaa acatagtgcc   1200
tatatttatt ctaaaaatat agacaaccta atagatttg aaagagaaat agatactact   1260 attttttgtaa agaatgctaa atctttttgct ggtgttggtt atgaagcaga aggattaca   1320 actttcacta ttgctggatc tactggtgag ggaataacct ctgcaaggaa ttttacaaga   1380
caaagaagat gtgtacttgc cggctaa                                        1407
```

<210> SEQ ID NO 18
<211> LENGTH: 2577
<212> TYPE: DNA
<213> ORGANISM: Artificial Sequence
<220> FEATURE:
<223> OTHER INFORMATION: Clostridium acetobutylicum adhE2 gene

<400> SEQUENCE: 18

| | | | | | |
|---|---|---|---|---|---|
| atgaaagtta | caaatcaaaa | agaactaaaa | caaaagctaa | atgaattgag | agaagcgcaa 60 |
| aagaagtttg | caacctatac | tcaagagcaa | gttgataaaa | ttttaaaaca | atgtgccata 120 |
| gccgcagcta | aagaaagaat | aaacttagct | aaattagcag | tagaagaaac | aggaataggt 180 |
| cttgtagaag | ataaaattat | aaaaaatcat | tttgcagcag | aatatatata | caataaatat 240 |
| aaaaatgaaa | aacttgtgg | cataatagac | catgacgatt | ctttaggcat | aacaaaggtt 300 |
| gctgaaccaa | ttggaattgt | tgcagccata | gttcctacta | ctaatccaac | ttccacagca 360 |
| attttcaaat | cattaatttc | tttaaaaaca | agaaacgcaa | tattctttc | accacatcca 420 |
| cgtgcaaaaa | aatctacaat | tgctgcagca | aaattaattt | tagatgcagc | tgttaaagca 480 |
| ggagcaccta | aaaatataat | aggctggata | gatgagccat | caatagaact | ttctcaagat 540 |
| ttgatgagtg | aagctgatat | aatattagca | acaggaggtc | cttcaatggt | taaagcggcc 600 |
| tattcatctg | gaaaacctgc | aattggtgtt | ggagcaggaa | atacaccagc | aataatagat 660 |
| gagagtgcag | atatagatat | ggcagtaagc | tccataattt | tatcaaagac | ttatgacaat 720 |
| ggagtaatat | gcgcttctga | acaatcaata | ttagttatga | attcaatata | cgaaaaagtt 780 |
| aaagaggaat | ttgtaaaacg | aggatcatat | atactcaatc | aaaatgaaat | agctaaaata 840 |
| aagaaaacta | tgtttaaaaa | tggagctatt | aatgctgaca | tagttggaaa | atctgcttat 900 |
| ataattgcta | aaatggcagg | aattgaagtt | cctcaaacta | caaagatact | tataggcgaa 960 |
| gtacaatctg | ttgaaaaaag | cgagctgttc | tcacatgaaa | aactatcacc | agtacttgca 1020 |
| atgtataaag | ttaaggattt | tgatgaagct | ctaaaaaagg | cacaaaggct | aatagaatta 1080 |
| ggtggaagtg | gacacacgtc | atctttatat | atagattcac | aaaacaataa | ggataaagtt 1140 |
| aaagaatttg | gattagcaat | gaaaacttca | aggacattta | ttaacatgcc | ttcttcacag 1200 |
| ggagcaagcg | gagatttata | caatttttgcg | atagcaccat | catttactct | tggatgcggc 1260 |
| acttggggag | gaaactctgt | atcgcaaaat | gtagagccta | acatttatt | aaatattaaa 1320 |
| agtgttgctg | aaagaaggga | aaatatgctt | tggtttaaag | tgccacaaaa | aatatatttt 1380 |
| aaaatatggat | gtcttagatt | tgcattaaaa | gaattaaaag | atatgaataa | gaaaagagcc 1440 |
| tttatagtaa | cagataaaga | tctttttaaa | cttggatatg | ttaataaaat | aacaaaggta 1500 |
| ctagatgaga | tagatattaa | atacagtata | tttacagata | ttaaatctga | tccaactatt 1560 |
| gattcagtaa | aaaaaggtgc | taaagaaatg | cttaactttg | aacctgatac | tataatctct 1620 |
| attggtggtg | gatcgccaat | ggatgcagca | aaggttatgc | acttgttata | tgaatatcca 1680 |
| gaagcagaaa | ttgaaaatct | agctataaac | tttatggata | taagaaagag | aatatgcaat 1740 |
| ttccctaaat | taggtacaaa | ggcgatttca | gtagctattc | ctacaactgc | tggtaccggt 1800 |
| tcagaggcaa | caccttttgc | agttataact | aatgatgaaa | caggaatgaa | atacccttta 1860 |
| acttcttatg | aattgacccc | aaacatggca | ataatagata | ctgaattaat | gttaaatatg 1920 |
| cctagaaaat | taacagcagc | aactggaata | gatgcattag | ttcatgctat | agaagcatat 1980 |
| gtttcggtta | tggctacgga | ttatactgat | gaattagcct | taagagcaat | aaaaatgata 2040 |

-continued

```
tttaaatatt tgcctagagc ctataaaaat gggactaacg acattgaagc aagagaaaaa     2100
atggcacatg cctctaatat tgcggggatg gcatttgcaa atgctttctt aggtgtatgc     2160
cattcaatgg ctcataaact tggggcaatg catcacgttc cacatggaat tgcttgtgct     2220
gtattaatag aagaagttat taaatataac gctacagact gtccaacaaa gcaaacagca     2280
ttccctcaat ataaatctcc taatgctaag agaaaatatg ctgaaattgc agagtatttg     2340
aatttaaagg gtactagcga taccgaaaag gtaacagcct taatgaagc tatttcaaag      2400 ttaaagatag atttgagtat tccacaaaat ataagtgccg ctggaataaa taaaaaagat     2460
ttttataata cgctagataa aatgtcagag cttgcttttg atgaccaatg tacaacagct     2520
aatcctaggt atccacttat aagtgaactt aaggatatct atataaaatc attttaa       2577
```